(12) United States Patent
Hein

(10) Patent No.: US 12,011,273 B2
(45) Date of Patent: Jun. 18, 2024

(54) METHOD AND DEVICE FOR THE TECHNICAL SUPPORT OF THE ANALYSIS OF SIGNALS ACQUIRED BY MEASUREMENT, THE SIGNALS HAVING A TIME- AND SPACE-DEPENDENT SIGNAL CHARACTERISTIC

(71) Applicant: Oliver Hein, Hamburg (DE)

(72) Inventor: Oliver Hein, Hamburg (DE)

( * ) Notice: Subject to any disclaimer, the term of this patent is extended or adjusted under 35 U.S.C. 154(b) by 0 days.

(21) Appl. No.: 17/572,300

(22) Filed: Jan. 10, 2022

(65) Prior Publication Data

US 2022/0218257 A1 Jul. 14, 2022

(30) Foreign Application Priority Data

Jan. 13, 2021 (DE) ..................... 10 2021 100 558.2

(51) Int. Cl.
*A61B 5/372* (2021.01)
*A61B 5/00* (2006.01)
*A61B 5/279* (2021.01)
*A61B 5/307* (2021.01)
*A61B 5/341* (2021.01)
(Continued)

(52) U.S. Cl.
CPC .............. *A61B 5/307* (2021.01); *A61B 5/279* (2021.01); *A61B 5/341* (2021.01); *A61B 5/346* (2021.01); *A61B 5/347* (2021.01); *A61B 5/352* (2021.01); *A61B 5/358* (2021.01); *A61B 5/36* (2021.01); *A61B 5/372* (2021.01); *A61B 5/7235* (2013.01)

(58) Field of Classification Search
CPC ................................. A61B 5/346; A61B 5/372
USPC .......................................................... 702/79
See application file for complete search history.

(56) References Cited

U.S. PATENT DOCUMENTS 6,778,852 B2 8/2004 Galen et al.
2002/0143263 A1 10/2002 Shusterman
(Continued)

OTHER PUBLICATIONS

Mercer et al.—Early Repolarization Syndrom—Jun. 30, 2016.
(Continued)

*Primary Examiner* — Nicole F Lavert
*Assistant Examiner* — Nicole F Johnson
(74) *Attorney, Agent, or Firm* — Gerald E. Hespos; Michael J Porco

(57) ABSTRACT

A method enables analysis of (e.g. bioelectric) signals acquired by measurement. The method provides N signals U for an observation space and each has a time- and space-dependent signal characteristic U. Digitized signals for a time period T have M time points and define an M×N matrix with M tuples of N signal values each. Signal values acquired at time t form an N-tuple $\overline{U}_t=(U_1, \ldots, U_N)_t$ in a signal space. The method acquires all combinations of k tuples from the M tuples, and calculates distances between all tuples. Distance values are calculated and define edge lengths of a (k−1) simplex (SIM) with one simplex assigned to each combination of k time points. Quantity characteristics of the simplex (SIM) are encoded into color values (COL), and displays the colors in a combinatorial time lattice (CTL). Each lattice point (GP) is displayed with the color encoded for the assigned simplex.

10 Claims, 18 Drawing Sheets
(14 of 18 Drawing Sheet(s) Filed in Color)

(51) Int. Cl.
*A61B 5/346* (2021.01)
*A61B 5/347* (2021.01)
*A61B 5/352* (2021.01)
*A61B 5/358* (2021.01)
*A61B 5/36* (2021.01)

(56) References Cited

U.S. PATENT DOCUMENTS

| | | |
|---|---|---|
| 2004/0002661 A1 | 1/2004 | Schreck |
| 2006/0258947 A1* | 11/2006 | Olson .................... A61B 5/339 600/512 |
| 2015/0220812 A1* | 8/2015 | Curington .............. G06V 20/64 382/154 |
| 2018/0360337 A1 | 12/2018 | Remes et al. |
| 2021/0000369 A1 | 1/2021 | Luksic et al. |

OTHER PUBLICATIONS

Richard I Verrier—Microvolt T-Wave Alternans: Pathophysiology and Clinical—Aug. 30, 2019.
Peter W Macfarlane et al.—The Early Repolarization Pattern—Jul. 28, 2015.
Elaine N Clark et al.—Automatic Detecton of end—Mar.-Apr. 2014.
Thomas Rostock et al.—High-density activation mapping of fractionated electrograms in the atria of patients with paroxysmal atrial fibrillation—Jan. 3, 2006.
L Aro Aspo—Microvolt T-wave Alternans—May 5, 2016.
German Office Action dated Nov. 23, 2021.

* cited by examiner

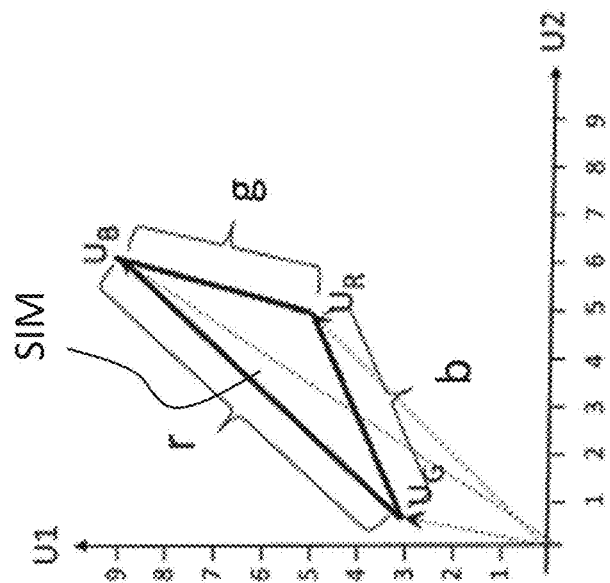
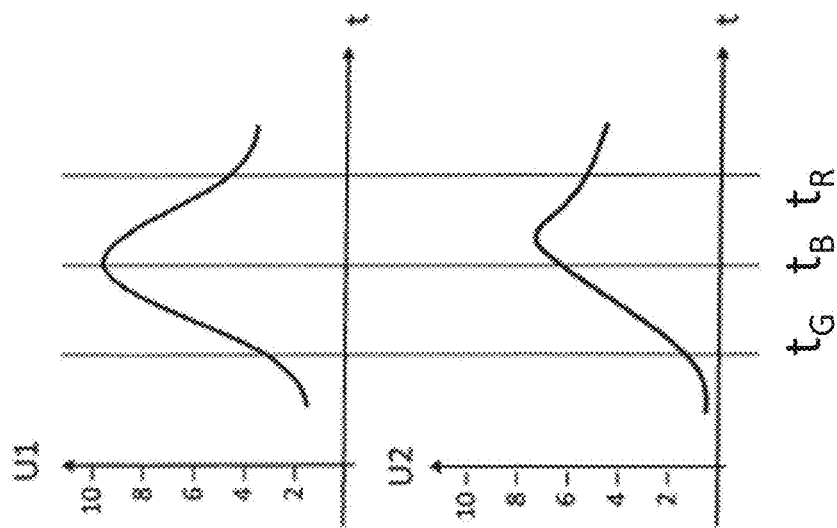
Fig. 3c
Fig. 3b
Fig. 3a

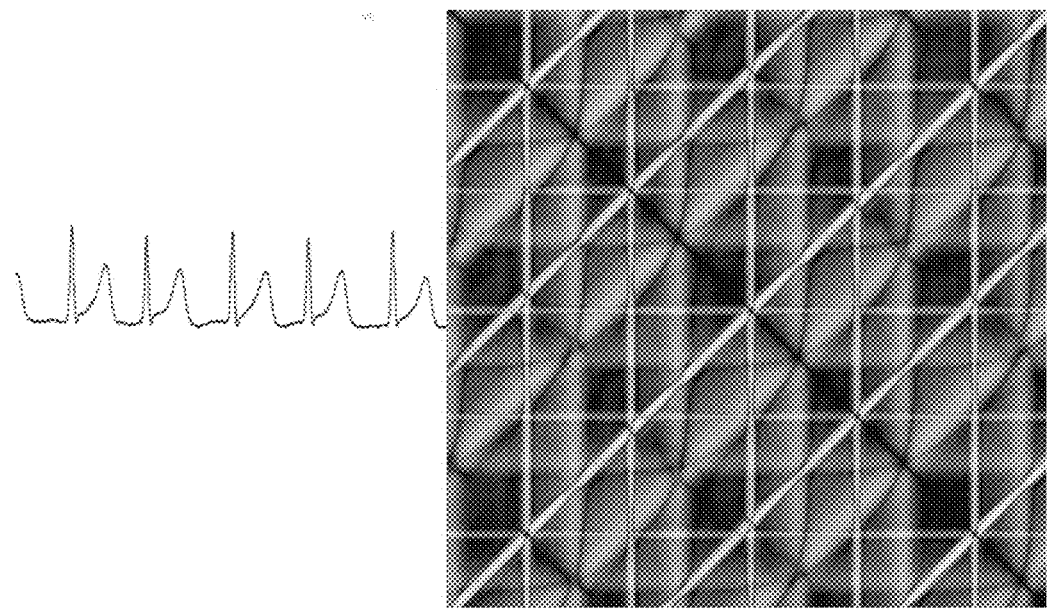
Fig. 5e
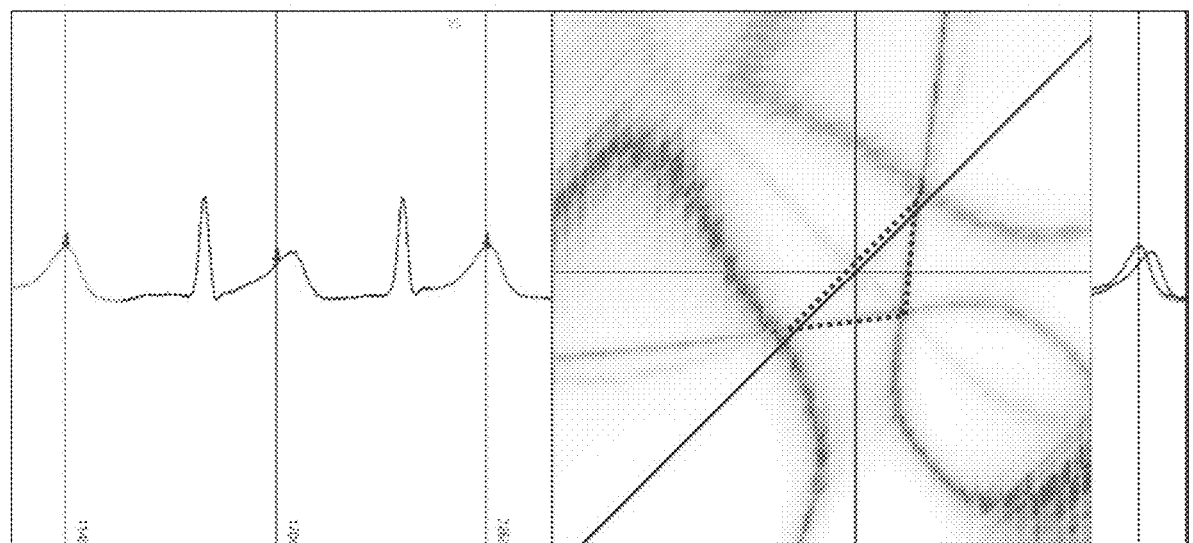
$t_G$  $t_B$  $t_R$  Fig. 5f

| 110 | Provision of N signals which have been acquired in a single-channel (N=1) or multi-channel (N>1) manner with respect to an observation space and thus each have a time-dependent and space-dependent signal characteristic (U), the N signals being provided in digitized form and for a predeterminable time period T comprising M time points and being capable of being represented as an MxN matrix (MAT) with M tuples of N signal values each, the N signal values acquired at the respective time t forming an N-dimensional signal vector $\vec{U}_t$ in an N-dimensional signal space; |

| 120 | Acquire all possible combinations of k (k≥2) tuples from the M tuples by acquiring k signal vectors $\vec{U}_1, \ldots, \vec{U}_k$ at k time points, and for each combination calculating all possible distances of the tuples from each other, whereby for each combination $\binom{k}{2}$ distance values (g, b, r) are calculated, which are interpretable as edge lengths of a (k-1) simplex (SIM), so that one simplex (SIM) is assigned to each combination of k time points ($t_G$, $t_B$, $t_R$); |

| 130 | Encoding at least one quantity characteristic of the respective simplex (SIM) to color values of a color valence (CV) on the basis of a color metric, and displaying the color valence in a combinatorial time lattice (CTL), wherein each lattice point (GP) of the time lattice represents a combination of k (k≥2) time points ($t_B$, $t_G$, $t_R$), to each of which one of the simplexes (SIM) is assigned, wherein each lattice point (GP) is displayed with that color valence (CV) which has been coded for the assigned simplex (SIM). |

METHOD AND DEVICE FOR THE TECHNICAL SUPPORT OF THE ANALYSIS OF SIGNALS ACQUIRED BY MEASUREMENT, THE SIGNALS HAVING A TIME- AND SPACE-DEPENDENT SIGNAL CHARACTERISTIC

CROSS-REFERENCE TO RELATED APPLICATION

This application claims priority under 35 USC 119 to German Patent Appl. No. 10 2021 100 558.2 filed on Jan. 13, 2021, the entire disclosure of which is incorporated herein by reference.

BACKGROUND

1. Field of the Invention

The invention relates to a method and a device for technically supporting the analysis of signals acquired by measurement (metrologically recorded signals), the signals having a time- and space-dependent signal characteristic. These include, for example, bioelectrical signals, comprising, in particular, physiological and medical signals or data. In particular, the invention relates to a method and a device which, on the basis of a cluster of signals, enable an overall visualization of the time- and space-dependent signal characteristics or properties, in particular a visualization of the spatio-temporal coherence of the signals or their data. Thus, the invention is also intended to be suitable for a technical support of the analysis of any kind of temporally as well as spatially recorded signals or data, which refer to a space of time (time span) and to a space of observation/measurement and thus can be understood as time- and space-dependent signals or data. In addition to the above-mentioned bioelectric signals, this also includes, for example, seismographic signals or signal data. Likewise, it can also be a matter of data series which have been recorded and are to be analyzed, e.g. as demographic data series, epidemiological data series or as econometric data series, in particular financial data series. Furthermore, this area includes eye-tracking data, which are collected, for example, in the context of psychological and neurological studies as well as in marketing.

In particular, the invention relates to areas of application in the field of physiology and medicine. There, bioelectric signals are usually recorded on or in the body of the patient (i.e. in the anatomical observation space) or on tissue parts as well as on the membrane level of single cells via electrodes, amplified, filtered and subsequently displayed on a screen or printout as electrical potential curves in order to be evaluated and diagnosed by a domain-specific expert, for example a specialist, such as a cardiologist, neurologist or physiologist. Typical bioelectrical signals recorded in this way are the ECG (electrocardiogram), the EEG (electroencephalogram), the EOG (electrooculogram), the EMG (electromyogram) or cell membrane action potentials.

The present invention is intended to provide a new method and a device, in particular a computer, executing the method for technically supporting the analysis of bioelectrical signals by domain-specific information extraction and information summarization. Furthermore, the invention also relates to a computer program product executing the method.

2. Field of the Invention

The usual methods and devices merely form the background and starting point for the inventor's realization that for differentiated diagnoses and prognoses (e.g., in the case of an ECG), multi-channel recordings are usually made on and in the patient's body. These can extend over a longer period of time, so that the usual diagrams can be very extensive with respect to the number of potential curves represented (e.g., in the case of a 252-channel ECG) and the span of the period of time considered. The interpretation/exploration of such multitudes of curves requires a very experienced expert and the large amount of time- and space-dependent data makes the recognition of characteristic patterns/morphologies in the overall view of all signals difficult or even impossible.

The problem is explained here in brief by showing three examples of typical problem cases (see FIG. 1a-1c). The first example (see FIG. 1a) is from the invasive treatment of atrial fibrillation by ablation procedures. Atrial fibrillation is the most common cardiac arrhythmia with a lifetime risk of about 25%. FIG. 1a shows a waveform cluster derived from the right atrium of the heart by using a 64-pole catheter in a bipolar fashion, i.e., a 56-channel acquisition of bioelectrical signals (electrograms EGM) in relation to the anatomical space of the heart is performed for 4.5 s. Thus, the set of curves comprises N=56 signals with a time- and space-dependent signal course or waveform. The difficulty is that the attending electrophysiologist must infer the course of myocardial excitation from these many waveforms. In particular, electrophysiologists must determine whether certain assumed mechanisms of an excitation disturbance are present. By knowing the position of the electrodes, the electrical excitation in the anatomical space (of the heart) can be deduced from the comparison of the signal courses, especially with regard to phase shifts between the channels.

The second example (see FIGS. 1b and 1c) relates to the occurrence of alternance of the T-wave and is based on the conventional scalar 12-lead surface ECG. As FIG. 1b shows, the course of the signal is divided into named sections. These have the rough morphology of a line (ST line), a wave (P wave, T wave, U wave), a peak (Q peak, R peak, S peak, together QRS complex) and their transitions are at specific points, e.g., the J point, the point of the transition of the QRS complex into the ST line. The exact determination of the J-point has a high importance in the context of the syndrome of early repolarization ("Early Repolarization Syndrome"—see Mercer at al., "Early Repolarization Syndrome; Mechanistic Theories and Clinical Correlates", published in "frontiers in Physiology", 2016). More detailed descriptions of individual sections are mostly descriptive, e.g., "high-positive T-wave." Curve I in FIG. 1c shows a recording over several seconds, which exhibits an alternance of the T-wave in its characteristic course. In the sections marked "A", the T-wave exhibits a rather low rise; in the sections marked "B", the T-wave exhibits a rather increased rise. Curve II in FIG. 1c shows the superposition of an A section with a B section. Through this, the alternance of the T-wave can be exemplified by an A-B comparison. The extent of the alternation in the morphology over time provides an indication of the possible occurrence of malignant tachycardia, which is one of the causes of sudden cardiac death. In Germany, approximately 65,000 people die of sudden cardiac death every year. This corresponds to 20 percent of all deaths caused by cardiovascular diseases. In order to accurately detect such an alternation, not only great experience is required on the part of the physician involved in the diagnosis; the signals displayed must also be recorded with as little interference as possible, since very small signal deviations must be analyzed. This issue is referred to as microvolt T-wave alternans (see chapter "Microvolt T-Wave Alternans: Pathophysiology and Clinical Aspects" by Richard. L. Verrier, in the textbook "Cardiac Repolarization" by N. El-Sherif (ed.), Springer publishing house, 2020).

Numerous supporting systems and methods are known to improve the representation of bioelectrical signals and their analysis:

A system and method for color-coding sections of an ECG are disclosed in U.S. Pat. No. 6,778,852 B2. A system and method for displaying ECG signals using a looped potential vector in a three-dimensional space representing the patient's anatomical space are disclosed in US Publication No. 2006/258947 A1, now U.S. Pat. No. 7,751,874 issued Jul. 6, 2010. A system and method for dynamic analysis of ECG data are disclosed in EP 1 284 645 B1.

The third example (not shown) relates to the long-term recording of an ECG. This is indicated in cases where the patient complains of paroxysmal tachycardia or syncope. In this case, an ECG must be recorded continuously for several days (even months and years). Printing and viewing a multi-channel ECG sampled at 1000 Hz over such long periods of time is not possible for obvious reasons (very large amount of data). In this case, it is necessary to condense the information relevant to the analysis over several temporal scales and represent it in condensed form. A system with mobile device for long-term recording of an ECG is disclosed, for example, in EP 3 415 083 A1.

The complexity described in the three examples is further increased when a holistic analysis across several signal classes is required. This is the case, for example, in somnology, where the above signals are assessed as a whole. FIG. 1d shows the simultaneous recording of EEG, ECG, EMG and EOG data from a somnological examination as it takes place in the sleep laboratory.

The examples mentioned are not exhaustive, but they clearly show how complex an analysis of biometric signals can be and that conventional visualizations of such signals, especially if they involve signal or curve sets, can overstrain even an experienced expert dealing with medical findings.

Therefore, it is the object of the present invention to propose a method and a device operating in accordance therewith for technically supporting the analysis of metrologically recorded (e.g. bioelectrical) signals, which advantageously overcome the problems of the prior art. In particular, the invention is intended to enable, in the field of medicine, an exact and unambiguous delineation of certain signal morphologies as well as an overall visualization of a host of biometric, in particular physiological and medical, signals, on the basis of their time- and space-dependent characteristics or properties, which significantly facilitates the interpretation of such signals for the purpose of better diagnosis. The invention is also intended, inter alia, to provide technical support for analysis with respect to the morphology of a waveform (see article "The Early Repolarization Pattern" by Peter W. Macfarlane et al., published in the "Journal of the American College of Cardiology", Vol. 66, No. 4, 2015 and in the article "Automatic detection of end QRS notching or slurring" by Elaine N. Clark et al., published in the "Journal of Electrocardiology" Vol. 47, pages 151-154, 2014). The invention is also intended to provide technical support for analysis regarding the collective behavior of a set of curves, e.g. their rotation or centrifugal pattern (see article "High-density activation mapping of fractionated electrograms in the atria of patients with paroxysmal atrial fibrillation" by Thomas Rostock et al., published in the journal "Heart Rhythm", Vol 3, No 1, January 2006).

The object is solved by the method and the device as disclosed and claimed herein.

SUMMARY

Accordingly, a method for technically supporting the analysis of signals acquired by measurement, in particular bioelectrical signals, which have a time- and space-dependent signal characteristic, is proposed with the following steps:

providing N signals (e.g., ECG, EEG signals) which have been acquired in a single-channel (N=1) or multi-channel (N>1) manner with respect to an observation space (e.g., the anatomical space of a patient) and thus in their entirety have a time- and space-dependent signal characteristic, the N signals being provided in digitized form and for a predeterminable time period T which comprises M time points, and being capable of being represented as an M×N matrix with M tuples of N signal values each, the N signal values acquired at the respective time t forming an N-tuple$(S)_t :=(S_1, \ldots, S_N)_t$. In practice, these are often N equal quantities, e.g., N voltage values. These allow an algebraic description in a vector space. They form an N-dimensional signal vector in an N-dimensional vector space;

acquiring all possible combinations of k (k≥2) tuples from the M tuples, e.g., acquiring k signal tuples at k time points $[(S)_1, \ldots, (S)_k]$ and, for each combination, calculating all possible distances of the tuples from each other, whereby for each combination $$\binom{k}{2}$$

distance values are calculated which can be interpreted as edge lengths of a (k−1)-simplex ((k−1)-SIM), so that a (k−1)-SIM is assigned to each combination of k time points;

coding at least one characteristic quantity for the respective simplex (SIM) (e.g. volume content, side area content (face areas), edge lengths, vertex angles) to a color characterized by its color valence. This is done by mapping the characteristic quantities to color values in a color space, e.g., the RGB color space. For the definition of color, color valence, etc., see standardization document DIN 5033-1. Subsequently, the colors are represented in a combinatorial time lattice (CTL), where each lattice point (GP) of the time lattice represents a combination of k (k≥2) time points, to each of which one of the simplexes (SIM) is assigned, where each lattice point (GP) is represented with that color (COL) that has been encoded for the assigned simplex (SIM). By color is meant not only chromatic colors, such as the colors of the rainbow, but also the achromatic colors, i.e., black, white, and shades of gray. The color valence of the respective color is determined by color values with which technical devices, in particular graphics cards, can be controlled for displaying the corresponding colors on monitors, etc. Thus, the technical color data are preferably color values for the primary colors or primaries of a color model or color space, such as the RGB color space or the YUV color model.

Color values are understood to be the coordinate values in a color space defined according to a color model, i.e., the color values of the (usually three) primary colors which cause the representation of the respective color by additive color mixing (i.e., vectorial addition). Preferably, the color values refer to an RGB color model, such as the CIE RGB color space. The color values are used as technical control parameters, e.g., for controlling a graphics card, in technical devices (e.g. PC, monitor).

Note on "Calculating all Possible Distances Between Tuples":

'Distance' means any function which satisfies the following condition for any two tuples:

$a(x,y) \geq 0$

The distance can be tightened to a distance by the following requirements:

$d(x,y) \geq 0$
$d(x,x) = 0$
$d(x,y) = d(y,x)$

Distance, in turn, can be tightened to a metric by the following requirements:

$d(x,y) \geq 0$,
$d(x,y) = 0$, exactly when $x = y$
$d(x,y) = d(y,x)$
$d(x,y) \leq d(x,z) + d(z,y)$, triangle inequality In the case of the Euclidean distance metric for the drawing plane N=2 or the visual space N=3, for k=3 these are the edge lengths of a triangle (points in general position/non-collinear) or for N=3, k=4 the edge lengths of a tetrahedron (points in general position/points not coplanar, here and in the following the general tetrahedron is always meant by tetrahedron), so that a set of measure numbers is assigned to each combination of k time points, in general the edge lengths of a (k−1)-simplex. Fundamental to the application is the general notion of distance. This is especially so because the datasets to be evaluated are not limited to uniform metric quantities, as are the voltage values in an ECG. General data sets contain more detailed information about the patient, such as his age, gender, laboratory chemistry values, information about concomitant diseases, etc. These data sets can also be evaluated with an ECG. These data sets can also be assigned a distance function or topology.

Note on the 'Simplex':

Decisive for the procedure disclosed here is the determination of all distance combinations. The geometrical illustration serves only the intuition. Admitted therefore are also "degenerated" triangles, where the three points are not in general position, but are linearly dependent. This is also valid for the "degenerated" tetrahedron, where the four points are not in general position, but linearly dependent. The focus is thus on combinatorial geometry. For the current application the intuition of classical geometric figures and solids is sufficient.

The distances or further measures (these are, for example, in the case of the interpretation as simplex: volume content, area content, edge lengths and/or angles) form the alphabet of the information coding. Subsequently, the transcoding of the distances or the continuing dimension(s) to a color and representation of the color in a combinatorial time lattice takes place, where each lattice point of the time lattice represents a combination of k (k≥2) time points and each lattice point is assigned the color that has been coded for the set of dimension(s).

The process thus essentially comprises three steps (as shown in FIG. 11):

Step 110: N metrologically recorded (e.g. bioelectrical) signals are provided, which are derived at different (anatomical) locations and which each have a time-dependent signal characteristic; the N signals are available in digitized form and for a predeterminable time period which comprises M time points, and can thus be represented, for example, as a matrix with M tuples of N signal values each; thus the signal values recorded at the respective time point form a measuring point in an N-dimensional space (signal space). The N signals can be provided, for example, by a database. In the case of bioelectrical signals, the signals or their data can originate from a database in which patient data are stored, or from the memory of a medical measuring device (e.g., for ECG, EEG).

Step 120: All possible combinations of k tuples out of the M tuples are now acquired, where k≥2; thus, k tuples are acquired at k time points and all distances of two tuples each are computed for each possible combination of 2 out of k tuples; this yields $$\binom{k}{2}$$

distance values; these distance values can be interpreted as edge lengths of a (k−1) simplex; thus, a simplex (e.g., a triangle or tetrahedron) can be assigned to each combination of k time points.

Step 130: Then, at least one quantity characteristic of the respective simplex (e.g., volume content, side area content, edge lengths, angles) is encoded into technical color information for a color according to a predetermined color metric (e.g., to RGB color values); and the colors encoded for all simplexes are represented in a combinatorial time lattice, wherein each lattice point of the time lattice represents a combination of k (k≥2) time points, to each of which one of the simplexes is assigned, and wherein each lattice point is represented with the color that has been encoded for the assigned simplex (SIM).

Thus, starting from a set of signal data (signal space) relating to metrologically recorded, time- and space-dependent signals (i.e., measurement signals which have been recorded at measurement points in a measurement space, e.g., on the anatomical body, over a period of time), a coding is carried out by which the trajectory of the signal data is converted to a representation in a color space which the human visual faculty, in particular the excellent visual faculty, can perceive. (i.e. measurement signals recorded at measurement points in a measurement space, e.g. on the anatomical body, over a period of time), a coding is carried out by means of which the trajectory of the signal data is converted into a representation in a color space which makes use of the human visual faculty, in particular the excellent perceptive faculty of colors and structures, and thus makes it possible to overcome the complexity and high information density prevailing in the signal space and to qualitatively record characteristic properties of the large signal quantity, such as, for example, the spatio-temporal coherence, very quickly and accurately, quasi "at a glance", and even to be able to evaluate them quantitatively. Thereby the metrologically obtained information of the data present in the signal space is preserved per se, but by coding the data to color values (control parameters e.g. for a graphics card, color printer, etc.) and arrangement of the corresponding colors in the time lattice (representation on an output medium, such as a screen) the data/information is transferred into a completely new and optically much faster perceptible representation (representation space). In certain cases, already an encoding to achromatic colors, i.e., to gray values, can be sufficient. In many cases, however, an encoding to chromatic colors is to be preferred:

First example case: In the case k=2, each combination of two (k=2) points in time is assigned a 1-simplex, in the geometric interpretation a distance, where its length is the characteristic size of the distance, and where each lattice point of the time lattice represents a combination of two (k=2) points in time, to which one of the distances is assigned in each case. In this case (k=2) an encoding with achromatic colors, i.e. grey values, is sufficient, whereby each lattice point is assigned/displayed with that grey value which has been encoded for the assigned distance. In the case k=2 and the Euclidean metric, this corresponds to the Euclidean distance matrix.

Second example case: In the case N=2 or N=3, each combination of three (k=3) points in time is assigned a 2-simplex (2-SIM), in its geometric interpretation in the form of a triangle, whose characteristic quantities include the area, the side lengths and/or angles, whereby each lattice point of the time lattice represents a combination of three (k=3) points in time (e.g., t G, t B, t R), to each of which one of the triangles is assigned. In this case (k=3) a coding with chromatic colors, i.e., color in the narrower sense, takes place, whereby each lattice point is assigned/displayed with that color which has been coded for the assigned triangle, e.g., by means of RGB color coding. The combinatorial time lattice thus consists of colored lattice points whose colors result from the color coding for characteristic quantities of the respective simplex (here, for example, the assignment of the three side lengths of the respective triangle to the three color values in RGB color coding). The resulting image makes the spatio-temporal coherence of the acquired signals intuitively detectable at a glance. Coherence here means the spatio-temporal relationship in the signal array. The coherence that can be intuitively grasped is conveyed by the color perception, which can recognise sections and patterns in the image of space-time. This ability of the visual system to recognize color coherent patterns is a remarkably optimized ability in the human observer in evolution, which enables the trained observer to recognize (detect) specific patterns in fractions of a second.

Third example case: In the case k=4, each combination of four (k=4) time points is assigned a 3-simplex, in its geometric interpretation a tetrahedron, whose characteristic quantities include the volume content, the side surface (face) contents, the edge lengths and/or angles, and wherein each lattice point of the time lattice represents a combination of four (k=4) time points, to each of which one of the tetrahedra is assigned, wherein each lattice point is represented with that gray or color value which has been coded for the assigned tetrahedron.

The procedure can be used for any higher levels (k>4).

In all cases, the characteristic quantities (parameters) of the respective simplex are calculated for the color coding, in particular gray and/or color value coding. In the case of a simplex (e.g. triangle or tetrahedron), the characteristic quantities which can be considered are in particular volume content, side area content, edge lengths and/or angles. In the case described in more detail further below where k=3, the signal values are taken at three points in time each and then three distance values are calculated which describe the side lengths of a triangle. In this case, the characteristic value(s) of the triangle can be determined to be its side lengths, area and/or angle. In particular, the three side lengths (i.e., distance values) are used to encode them to color values of the primary valences (coordinates in the color space). For this purpose, a predetermined color metric, such as the RGB color metric, can be used. For example, the side lengths corresponding exactly to the distance values are first scaled to a predefinable range of values, e.g. [000, . . . , 255]. Then, these scaled values are encoded into the color values of a corresponding color valence using the predetermined color metric (e.g., RGB, HSV, etc.). The calculated color values can be used, for example, to control a graphics card.

The representation of all calculated color values (color valence) is done in the combinatorial time lattice/grid, where the combinatorial time lattice has at least two orthogonal time axes, each referring to the first and last time point of time points. For three pairwise distinct time points, there must always be one time point between the two other time points. The specification of the location of this intermediate point is made with respect to the two boundary points as an affine combination of the two temporal boundary points (more precisely as a convex combination) and thus in barycentric coordinates. For most evaluations it is advantageous to place the temporal intermediate point exactly in the middle between the two temporal boundary points, i.e. on (0.5, 0.5). By this, all acquired combinations can be represented in the combinatorial time lattice, and in a plane, where each lattice point of the time lattice represents one of the calculated colors, i.e., their color values. If, for example, a time span of 2 seconds is recorded at a sampling rate of 1000 Hz, the time lattice will have a total of 2000×2000=4 million lattice points. As a result, gray-scale or colored patterns are formed in the displayed time lattice, which impressively illustrate the spatio-temporal coherence of the acquired signals at a glance. The aforementioned example also illustrates one of the advantages of modern graphics hardware and one of the capabilities of the human visual system, namely the ability to perceive information uniformly across many different scale ranges. For example, the representation and perception of the above-mentioned image of 2000×2000 lattice points does not take place at the level (scale) of individual pixels, since the currently technically common displays allow a Full HD resolution, i.e. 1920× 1080, which is lower than that of the image. Furthermore, the pixel density is such that no individual pixels are perceptible. What is still perceptible, however, is the general structure in the image, which proves robust even with repeated scaling. This is even more impressive for much larger images. Standard recordings of a 12-channel ECG are made over 10 seconds and result in images of size 10000× 10000 at a sampling rate of 1000 Hz.

The invention addresses the above-mentioned problems by processing the provided bioelectric signals or signal data and transforming them into a completely new representation in such a way that, in particular, time- and space-dependent characteristics (spatio-temporal coherence of N signals) can be recognized quickly and clearly over several time scales. The patterns recognized in this process are encoded in an alphabet.

In particular, the invention produces the following effects:
Translation of the variation/dynamics of a set of N signals, N≥1, by a set of measures/indexes, which are basically distances in the signal space, but can also be higher measures, e.g. areas, volumes, etc. Each possible combination of k, k≥2, time points is assigned at least one measure/index.
Conversion of the measures/measured values into a multiway array (multidimensional matrix).

Transcoding of the measurement values into color values (coordinates in the color space) and representation of the corresponding colors in a combinatorial time lattice as an image.

Multiscale summarization of data-intensive time series based on visual perception (especially color perception).

Detection of specific signal morphologies and encoding of the morphologies into symbols from a symbol alphabet.

The invention is based on the following essential findings:

It is possible to fully describe the dynamics of state changes by considering all combinatorial possibilities of k, k≥2, time points each from the observation period.

Each combination corresponds to k system states. These are related, e.g., by their respective distances.

A high granularity is achieved by forming all possible combinations of k time points each; a combinatorial time lattice designed by the inventor himself is suitable for this purpose.

The occupation of the time lattice by e.g. distance values is transformed into a visual perception by the transformation into a suitable color space. The human visual system is the most highly developed system for information evaluation. Human visual perception has highly developed pattern/structure recognition functions. This makes intuitive and very fast analysis possible. Current technology has specially developed hardware, e.g. graphic cards, which enables very fast and efficient processing of color and graphic information.

By entering the color values into the combinatorial time lattice, the characteristics/patterns (spatio-temporal signal coherence) based on the relations of the sampled values come to light, which are clearly recognizable even in the case of very many signals/channels.

BRIEF DESCRIPTION OF THE DRAWINGS

The patent or application file contains at least one drawing executed in color. Copies of the patent or patent application publication with color drawing(s) will be provided by the Office upon request and payment of the necessary fee.

The invention and the advantages resulting therefrom will be described in further detail below with reference to examples of embodiments, with reference to the accompanying drawings which schematically illustrate the following:

FIGS. 3a, 3b and 3c illustrate the calculation of distances between three signal values (signal vectors spanning a simplex in the form of a triangle) and the coding of the distances (side lengths) to color values, here using the example of a multi-channel signal (signal array, N=2).

FIGS. 5a through 5f show in detail such patterns forming in the time lattice, here for the analysis of a single-channel signal (a, b idealized ECG, c-f real ECG).

FIG. 11 is a flow chart for the method according to the invention.

DETAILED DESCRIPTION

Figure 1A:
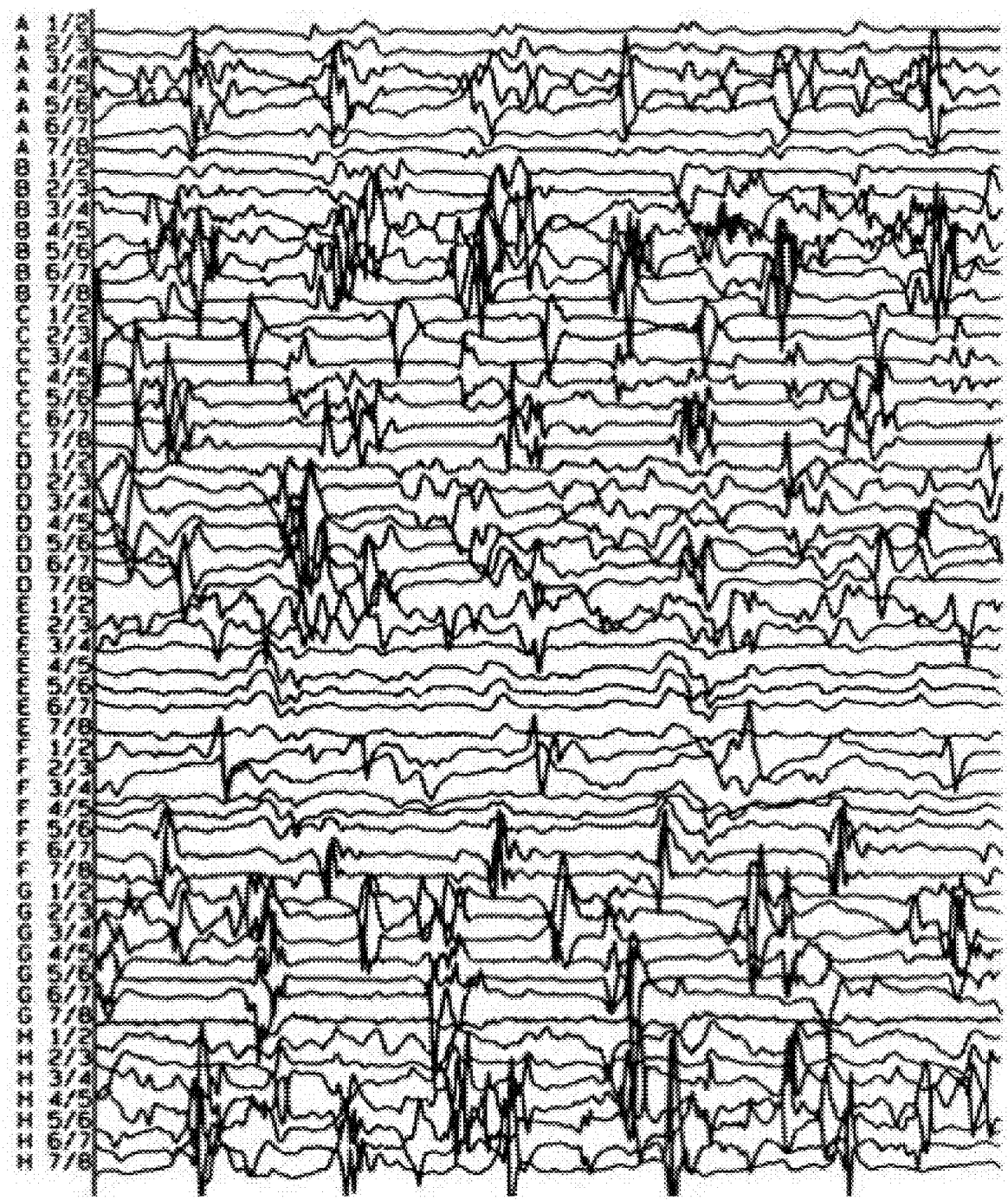
FIG. 1a shows a waveform cluster derived from the right atrium of the heart by using a 64-pole catheter in a bipolar fashion, i.e., a 56-channel acquisition of bioelectrical signals (electrograms EGM) in relation to the anatomical space of the heart performed for 4.5 s FIGS. 1b and 1c relate to the occurrence of alternance of the T-wave and is based on the conventional scalar 12-lead surface ECG.
Figure 1B:
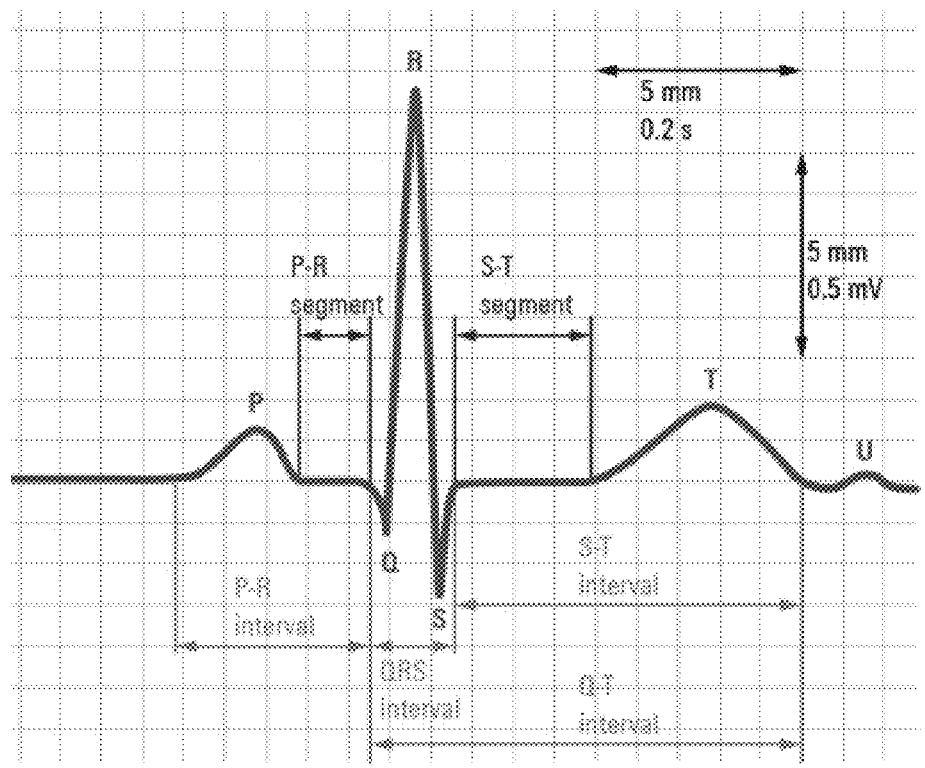
FIG. 1d shows the simultaneous recording of EEG, ECG, EMG and EOG data from a somnological examination as it takes place in the sleep laboratory.
Figure 1C:
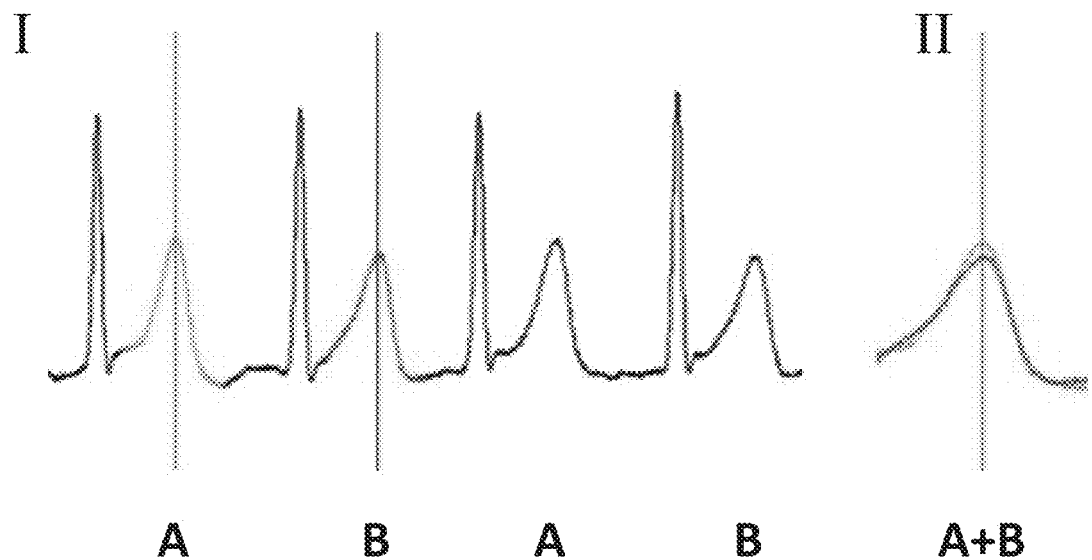
Figure 1D:
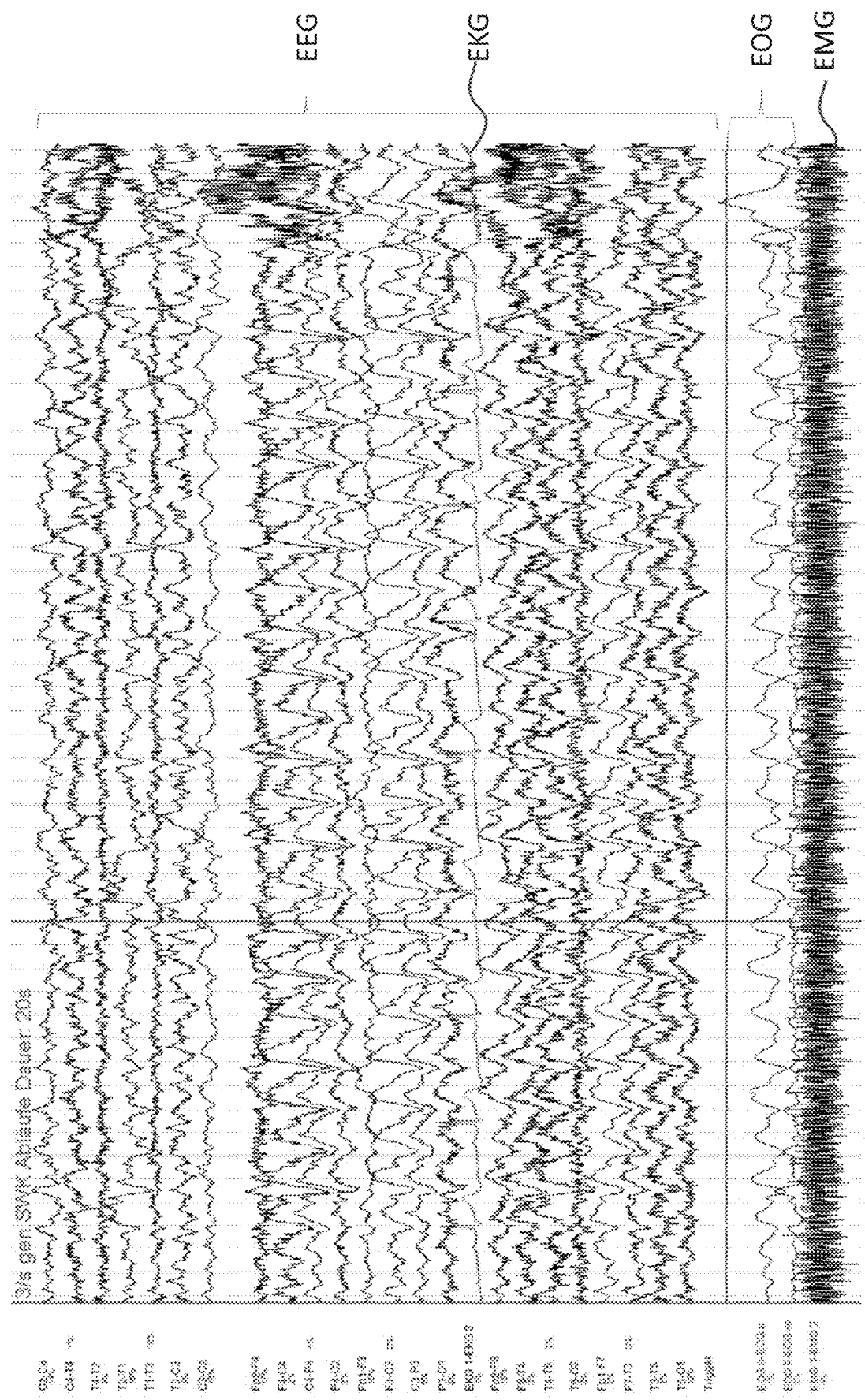
Figure 2A:
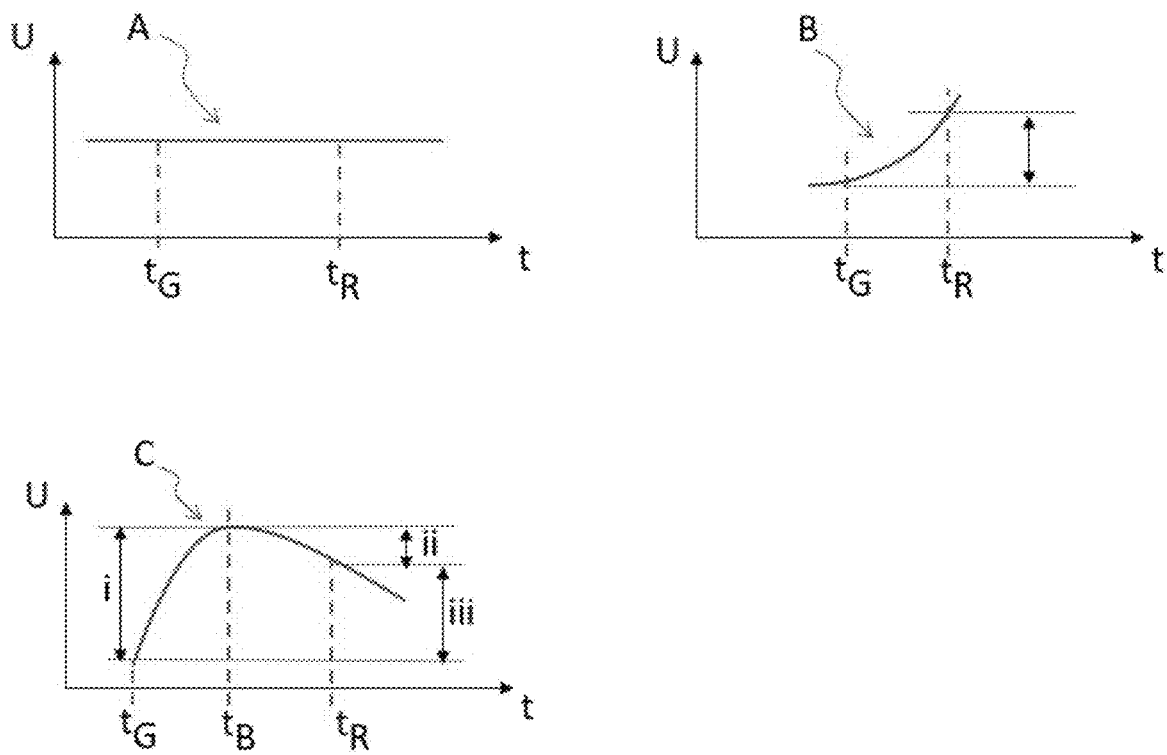
FIG. 2a illustrates one aspect of the invention, namely the detection of signal values, here using the example of a single-channel signal (N=1), at two or three respective points in time (sampling points), each with different signal characteristics A, B or C: constant, rising or rising and falling.
Figure 2B:
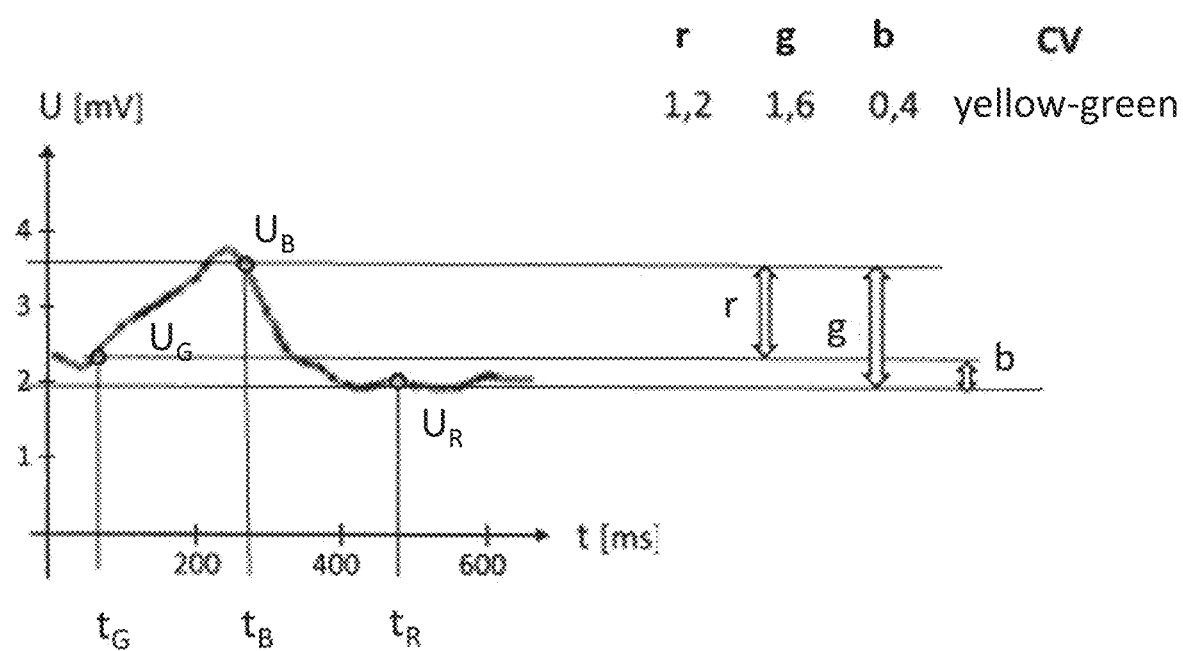
FIG. 2b illustrates a further aspect of the invention, namely the calculation of distances between three signal values in each case and the coding of the distances into color values, here using the example of a single-channel signal (N=1).

Reference is first made to FIGS. 2a and 2b, which illustrate a first aspect of the invention using a single channel ECG signal as an example.

As illustrated by sketches A-B in FIG. 2a, already with three time points and the three signal values (samples) obtained at the three time points, a differentiated statement about the relative signal characteristics can be made. This is motivated in two steps:

In the first stage, the question of a change in the temporal signal course arises. To detect a change in the signal, two points in time are sufficient, e.g. t G and t R (see signal waveforms A and B). If the signal values are different at two different points in time, a change has obviously taken place. There is also the possibility that the signal value has changed in the meantime and then returned to the initial value. However, this is unlikely for steady signals and short time intervals. The combined view from the signal value change over the time change is the approach in classical analysis. Here, the limit value of the difference quotient from signal value change and time change is considered.

However, it is not clear from the change whether this occurred monotonically, in the sense of a mere rise or mere fall, or by a combination of rise and fall, subsequently referred to as variation. This can be determined if a further point or third time tB is considered between the two end points of the interval (intermediate time) and the three changes associated with it are related to each other (see signal waveform C). This relationship of the three changes is expressed in three distances or signal value differences and is now calculated numerically as well as communicated visually. In doing so, methods of triangular geometry can be used. The invention makes use of this insight.

FIG. 2b shows the application of this principle to only one channel of an ECG (today's sampling rates are at least 1000 Hz and quantizations of e.g., 24 bit). First, the signal values or sample values UG, UB, UR are recorded at any three times tG, tB, tR. In the example shown, the time points are each about 200 ms apart, with the middle time point tB (B stands for "between") being somewhere in the middle between the other two time points. Preferably, the middle time point should (but need not) be exactly halfway between the two outer time points. This gives a combination (or set) of three (equidistant) time points. The time intervals as well as the location of the time points are varied so that all possible combinations are captured. For example, if the signal data is to be analyzed in a time window of 1000 ms and the signal was sampled at 1000 Hz, then there are a total of 1 billion (1000×1000×1000) possible combinations of three time points each.

As FIG. 2b shows, it can already be recognized by means of three sampling points of a signal (here using the example of a 1-channel ECG) that the signal curve first increased by the amount r=1.2 mV and then changed again by a similarly high amount g=1.6 mV. That there was first a rise and then a fall in the signal can be seen from the fact that the third magnitude b=0.4 mV is very small; thus the signal must have fallen again in the time span between tB and tR. Furthermore, it can be seen from the fact that the distances r and g are approximately equal, that rise and fall occurred almost symmetrically. Therefore, even three intervals can tell us very much about the dynamics of the signal in the time period tG to tR. If the three time intervals are very close to each other, the granularity/temporal resolution is increased. By shifting the time points, the entire observation period is covered, and the offset determines the granularity/temporal resolution. All possible combinations are covered: For a viewing period of e.g., 10,000 ms (=10 s) and a sampling rate of 1000 Hz, i.e., a temporally constant distance of 1 ms between two consecutive measurement points, a total of one trillion (10,000×10,000×10,000) possible combinations of three time points each are captured. The three distances r, g, b calculated for each combination are normalized if necessary and then converted into a color means of color coding. In the example shown, the calculated distances r=1.2 mV; g=1.6 mV and b=0.4 mV are then normalized to fit within the range of values [000-255]. The normalization is performed with respect to the measurement interval, i.e., the maximum of all distances determined in the time interval, or with respect to the measurement frame, i.e., the voltage interval within which the measured values lie physiologically. The resulting normalized values [120, 160, 40] represent the color values (COL) or color components of a corresponding color (color valence CV, a vector in color space) and, in this example, when printed or displayed via a color display, lead the viewer to a color impression that he perceives as a yellow-green color valence. This color coding is performed for all combinations. The calculation and processing of corresponding amounts of data is easily feasible with today's modern processors and memory volumes. It should be noted that the full density of combinations is not required for the necessary analysis, but the essential information takes place at a much higher level of lattice width and compression (scale space).

It should also be noted that the principle can be generalized by interpreting the three distances r, g, b as side lengths of a triangle, and thus other characteristic quantities of the triangle, such as area or angle, can also be encoded as color or color valence (chromatic or achromatic). For each combination of three time intervals there is a representative triangle. If, for example, one takes the area of the respective triangle and codes its value by means of a gray scale (i.e., scale for the achromatic color range), one obtains a gray value for each combination, which does not have the amount of information as the above color values (coded side lengths), but which can be quite sufficient to characterize the respective information of interest with sufficient precision.

Figure 2C:
FIGS. 2c and 2d illustrate the multi-channel (N=12) acquisition of signal values and evaluation in a time domain (T=10 s with M=10000 time points) and representation in a matrix.
Figure 2D:
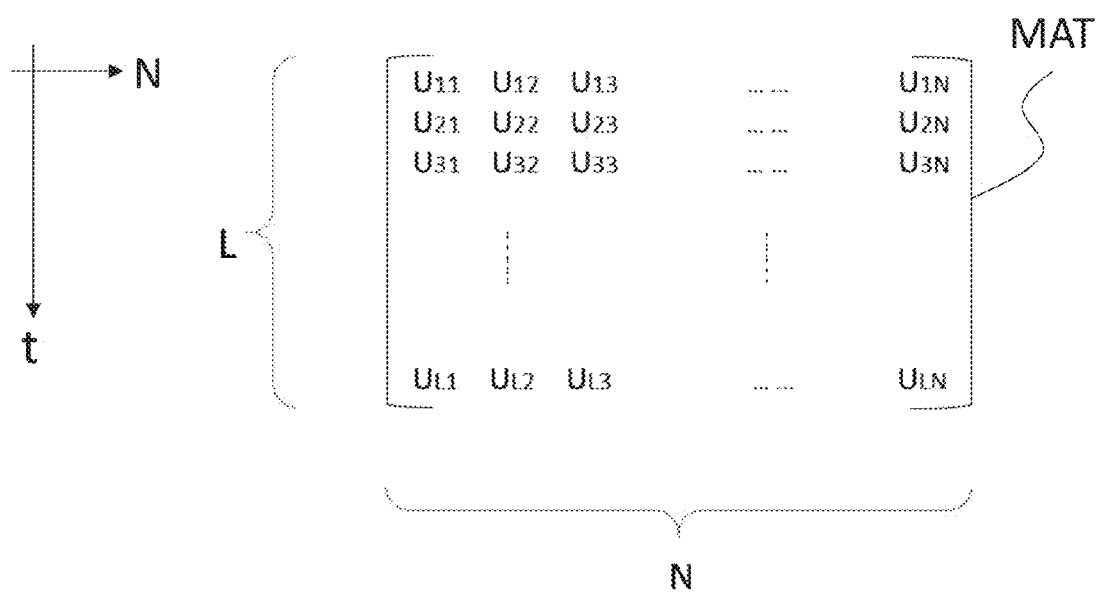

If a multi-channel signal measurement is performed (e.g., on N=12 channels), then the temporal sampling and acquisition of the signal values can be illustrated in the form of a matrix. FIG. 2c shows an example of the signal waveforms of a 12-channel ECG over a time period of T=2000 ms. When sampled at 1000 Hz, N=12 signal values are obtained for each M=2000 time points. As FIG. 2d shows, the signal values can be entered into an M×N matrix MAT, whose M rows form tuples with N=12 signal values each. Each tuple thus contains the signal values acquired at the respective time point and can thus be understood and further processed as a signal vector (see also FIG. 3b described below).

FIGS. 3a, 3b and 3c now describe in detail how the principle of the invention can be applied to multi-channel (N>1) signals: In FIG. 3a, the signals U1 and U2 of a two-channel (N=2) ECG are shown as an example. At each time point (sampling point) N=2 signal values are present, which can be understood as a 2-tuple or ordered pair and can be represented in vectorial form in an N-dimensional space (here N=2). This is easily possible for N=2 in the drawing plane. For the three sampling or time points, three vectors UG, UB, UR, which span a simplex SIM in the form of a triangle, result here (see FIG. 3b). As characteristic quantities the side lengths are to be considered (area or angle of the triangle remain out of consideration in this example).

The distances r, g, b of interest now each correspond to a distance of two vectors, e.g., b=‖UG−UR‖. The three distances or side lengths of the triangle SIM are now to be used for the coding according to the invention. The numerical examples in FIG. 3c illustrate this by way of example: first the three distances r, g, b are normalized according to a predeterminable range of values, here from 8 bits (000 to 255), and then converted according to a color coding, here RGB coding, into three color values COL for a color (color valence CV). If all three distance values are (approximately) of the same size (r≈g≈b), i.e., the triangle is approximately equilateral, then this results in colors on the gray scale, which range from black [000, 000, 000] to white [255, 255, 255]. If the three distances are different, then (real chromatic) colors result, i.e., no gray values:

if b<r, g and r~g, then yellow color values are obtained;
if r<g, b and g~b, then cyan color values are obtained;
if g<r, b and r~b, then magenta color values are obtained.

Thus, if two distances are (exactly) equal and one distance is smaller, the result will be pure yellow, cyan or magenta color values according to additive color mixing (see https://en.wikipedia.org/wiki/Additive_color). If the smaller distance value is very small compared to the other two distance values of approximately the same size, then this results in an intense yellow, cyan or magenta color; if the smaller distance value is not particularly small compared to the other values, then this results in an unsaturated color in each case (see FIG. 3c).

The essential interpretation of the distance values is based on the relative smallness of one of the three values compared to the other two values. Such a constellation occurs, for example, when the value at the first time point and at the third time point are the same and when the value at the intermediate time point is different. This constellation is characteristic for an elongation, see FIG. 2b. The deflection (elongation) always refers to three arbitrary points in time. If there are three different times in pairs, there must always be a time between the two remaining times. This intermediate time point has a deflection with respect to the two temporally adjacent points. Thus the null position is not global but always seen in relation to the arbitrary selection of two points of time. Thus there is no precondition (presupposition) of a base line. Should this exist, it will show up in the global view of all local three-point-relations. Thus any elongation is always perceived in a global context. This perception is a direct visual color perception.

According to the invention, the distance values calculated and normalized for all combinations are now converted into technical color data or color values and the corresponding color valences are visualized in a combinatorial time lattice designed by the inventor for this purpose. In this, patterns are formed which are characteristic for time- and space-dependent characteristics or properties of the detected signals or the signal array.

Figure 4B:
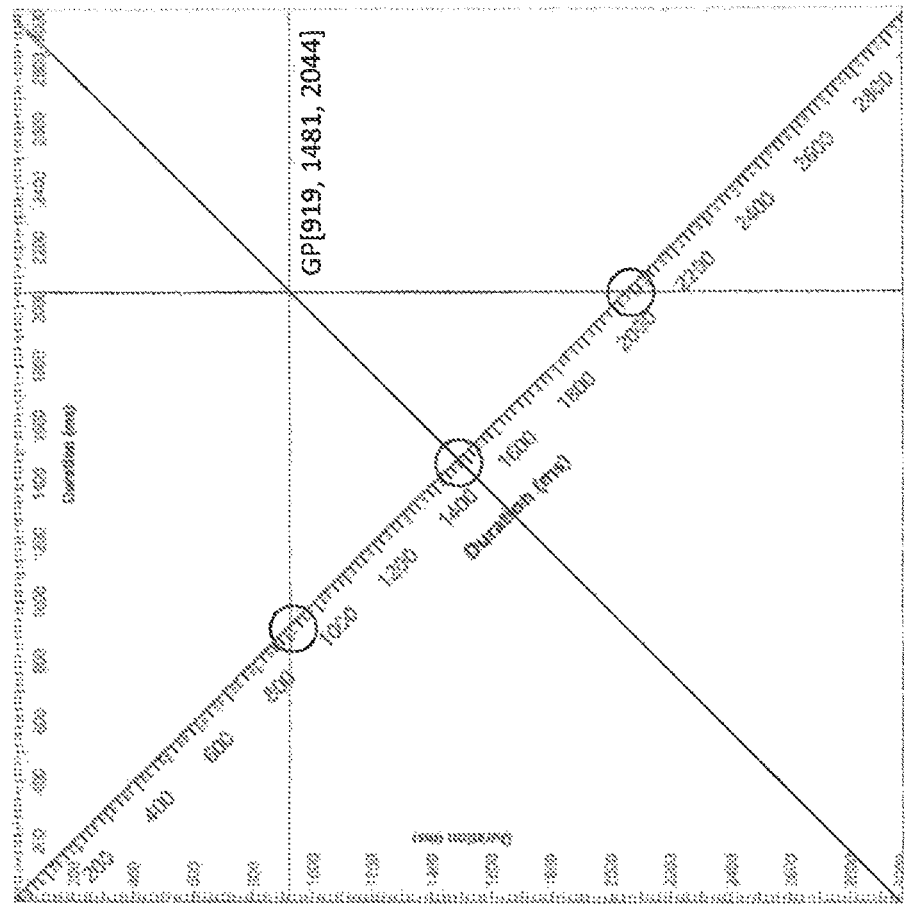
FIGS. 4a and 4b illustrate yet another aspect of the invention, namely, entering all calculated color values into a combinatorial time lattice, resulting in patterns that are characteristic of time- and space-dependent manifestations or properties of the detected signals or signal array.
Figure 4A:
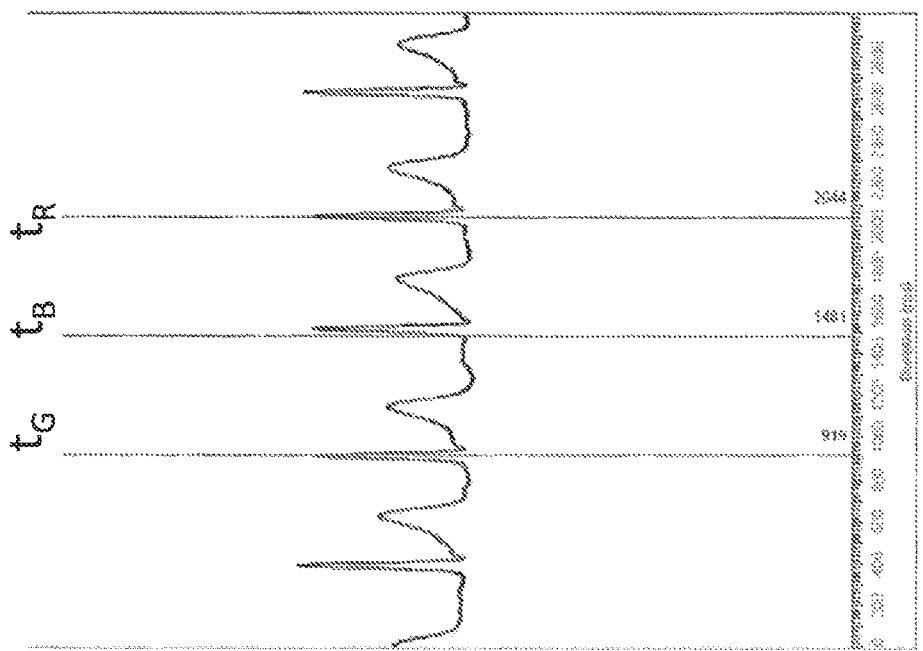

FIGS. 4a and 4b illustrate the structure of a combinatorial time lattice (CTL) according to the invention and the visualization of the distances r, g, b calculated in each case as color values COL for a color. FIG. 4a shows an example of a single-channel signal waveform U in which the signal values are acquired at three times tG, tB and tR and the three distances r, g, and b are calculated from them (similarly as described above with reference to FIG. 2b). In the present case, the combinatorial time lattice CTL (see FIG. 4b) consists of three time scales, although the number of dimensions can be increased, two of which are orthogonal and span a plane. These two time scales refer to the outer time points tG and tR, respectively. The third time scale, the main scale, lies on the bisector and can represent all three time points tG, tB and tR. The value of tB is fixed in normalized barycentric coordinates of the time points tG and tR and is thus a value pair of $[0,1] \times [0,1]$. All time points between tG and tR including the boundary time points are possible. For the barycentric coordinates [0.5, 0.5], the time point tB is exactly between tG and tR. The time points tG, tB and tR are thereby read by cursors. The tG-cursor intersects the tG-scale at time tG and runs axis-parallel to the tR-scale. The tR-cursor intersects the tR-scale at time tR and runs parallel to the axis of the tG-scale. The tB-cursor passes through the intersection of the tG-cursor and the tR-cursor. In the case where tB is exactly midway between tG and tR, the tB-cursor is orthogonal to the third time scale. For each combination the three time points can be read from the main scale and each temporal combination can be assigned a lattice point GP, which in turn can be assigned the color valence CV of the calculated color values (cf. FIG. 2b). The main time scale divides the time lattice into two halves. For the present evaluations, only the area above the main time scale is considered for the time being.

In the example from FIG. 4, a lattice point GP is set at tG=919 ms and tR=2044 ms; the time tB=1481 ms results from the center position. At this lattice point GP the distances of the acquired and normalized samples are now entered in coded form as color values COL, which in this example are determined by the RGB values [240; 050; 235], because the samples at tG and tR are very large and approximately equal in size, while the mean sample at tB is very small. This then results in a color valence in the yellow range. The color coding presented here can also be explained in more detail with reference to FIG. 2b already described:

In the example shown in FIG. 2b (very simplified) the following distance values were calculated: r=1.2 mV and g=1.6 mV and b=0.4 mV. These values can be transformed into a desired range of values by normalization, e.g. into the range of values [0 . . . 255], which is used for the identification of colors according to the RBG colorimetry. This results in the following normalized values r=120 and g=160 and b=40 (where 255 is the max. permissible value). For the set of all time points to be determined, the distance values are normalized to the maximum distance of all distances and thus lie in the range [0,1]. This range is then scaled to the range [0, 255]. The interpretation of the triple [120, 160, 40] in the RGB color space and output on a color display or color printer results in a corresponding color stimulus for the viewer and, as a consequence, a color valence and a color sensation. The color or the color valence is then entered in the combinatorial time lattice CTL at the location of the lattice point LP.

Technically, the visualization is implemented by a graphics card (e.g. of a PC) controlling a screen/display in such a way that in the image lattice (=time lattice) the corresponding image point (lattice point) appears in the calculated color, here e.g., with the color values COL=[120, 160, 040], with whose representation the viewer perceives a corresponding yellow-green color valence CV.

This procedure is carried out for all lattice points. The amount of data to be calculated can be very large, since the lattice of the time lattice CTL results from the max. number of sampling points which occur in the observation period: At a sampling frequency of 1000 Hz, the sampling points are spaced apart by 1 ms, so that for an observation period of 10 s, $10 \times 1{,}000 = 10{,}000$ sampling points must then already be taken into account and the total image of the time lattice CTL has $10{,}000 \times 10{,}000 = 100$ million lattice points (image points). This means that even with a relatively short observation period, a very large amount of data must be acquired (samples) and calculated (distances) as well as normalized and coded (RGB colorimetry). However, thanks to today's very powerful graphics cards and computer systems, this is no longer a challenge and can even be done in real time or quasi-real time. The inventor himself has created an executable program for this purpose.

The invention can be applied to any type of metrologically recorded (e.g. bioelectric) signals and provides a color visualization that simplifies the analysis, especially when there are multitudes of signals or data (multi-channel derivation). The fields of application are manifold and can be, for example, in the field of seismology, demography or economics. In the field of medicine, the applications cover, for example, the support of the analysis of ECG, EEG, EMG, EOG, and AP (Cell membrane action potentials) which can significantly improve diagnostics in particular. However, non-diagnostic investigations, such as epidemiological studies, can also benefit from the invention.

Due to the invention, in particular the time- and space-dependent characteristics or properties of the signals or data clearly emerge in the combinatorial time lattice in the form of patterns in the combinatorial time lattice, the signals or data clearly emerge in a completely new way, which in particular presents the spatio-temporal coherence of the signals/data to be analyzed quasi at a glance. And speed in the intuitive acquisition of signal characteristics is particularly necessary when there is no possibility for a longer analysis. This is the case, for example, in cardiology in the electrophysiological examination (EPU) and/or in an ablation procedure. Here, the treating electrophysiologist has to decide in seconds/minutes whether or not to perform obliteration of the myocardial tissue at a site in the heart. It is obvious that the required information from the set of curves (see also FIG. 1) must be displayed as intuitively as possible.

Figure 5A:
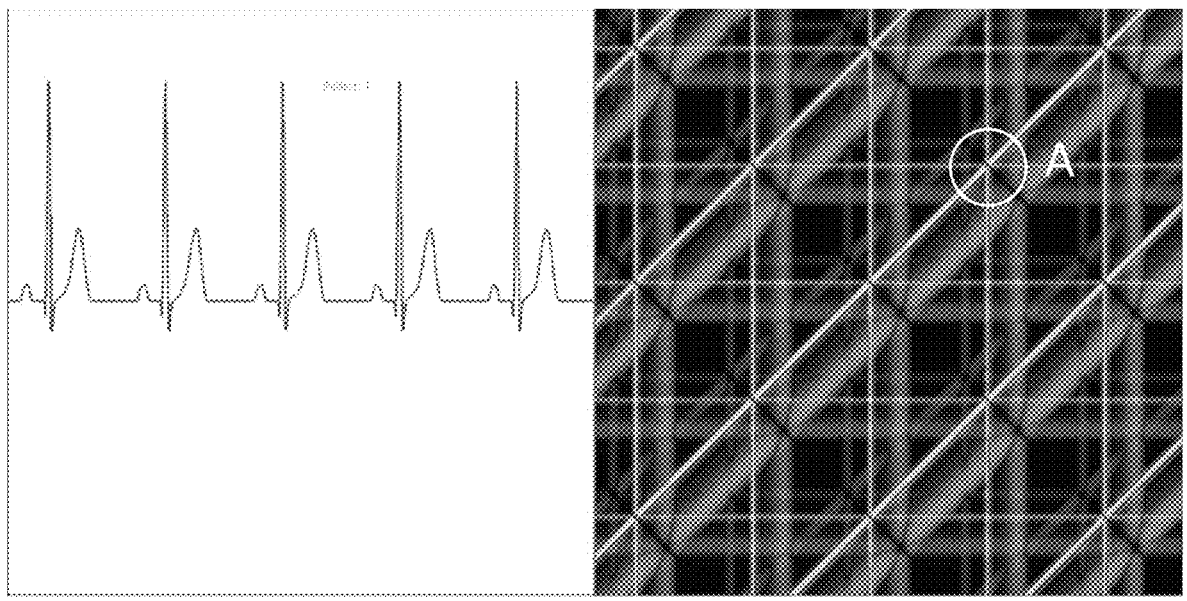
Figure 5B:
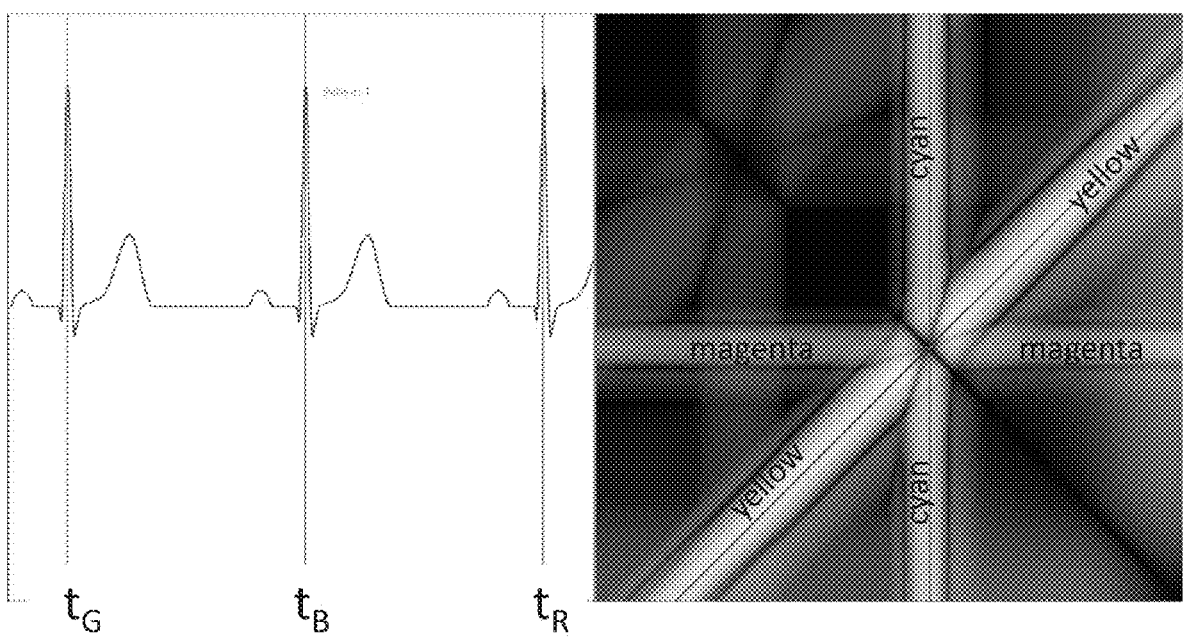

A further functional area relates to the detection of (disease-) specific patterns in the signals, including signal interference (noise). To illustrate the patterns, we refer to FIGS. 5a-f, which show in detail such patterns forming in the time lattice using the example of a single-channel ECG, here for the analysis of a single-channel signal U (N=1):

FIGS. 5a and 5b refer to a single-channel (constructed) ECG with an idealized course, i.e. to an interference-free, stable signal (left half of the figure), in order to explain the principal structure of the pattern calculated and represented according to the invention (right half of the figure) and its structure. In FIG. 5a, one can clearly see a pattern characterized by intersecting bar-shaped color lines. The 45° diagonal in the time lattice represents the main time scale, i.e. it is the time axis for tG, tB and tR (compare FIG. 4). In FIG. 5b, the structure of the pattern can be seen in a magnified view of area A. As far as the perception of the overall representation is concerned, human color perception very efficiently suppresses small inhomogeneities and enhances the perception of homogeneous areas.

Figure 5C:
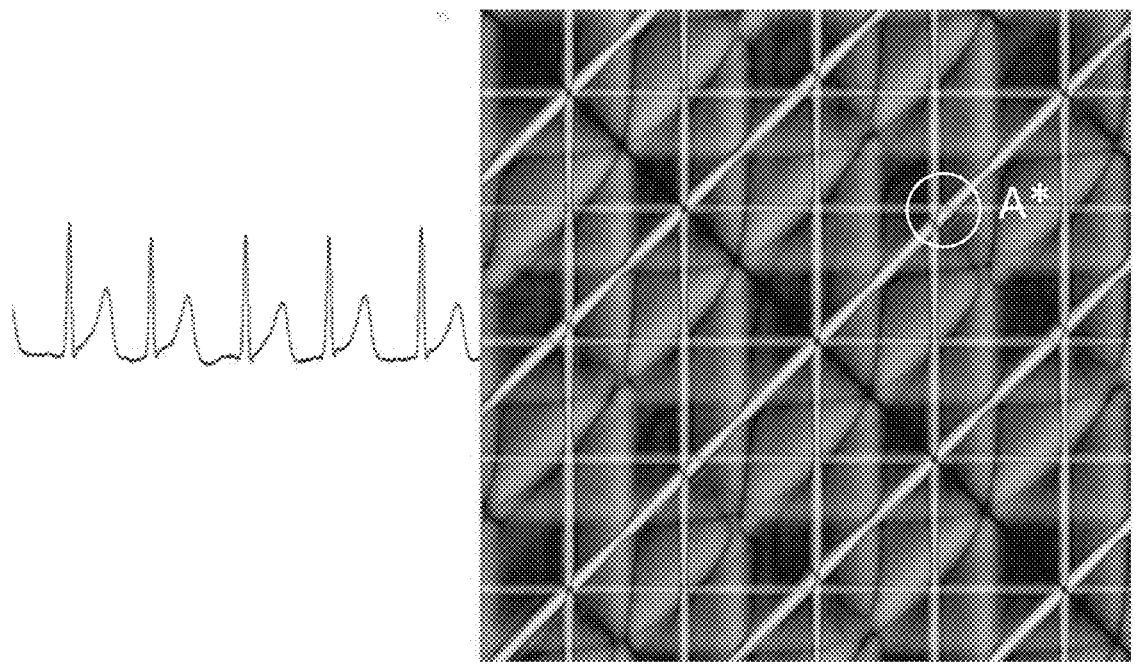

Looking at both FIGS. 5a and 5b, the first thing that stands out is the rectangular lattice structure. This structure decomposes into three sub-grids, which correspond to the three main deflections, P-wave, R-wave and T-wave. The three sub-grids/lattices differ in their brightness. The relative brightness corresponds to the relative voltage level (Voltage) of the individual waves and spikes. Each lattice consists of three axes, which are clearly separated by color. The vertical axes A1 are cyan, the horizontal axes A2 are magenta and the oblique axes A3 are yellow. Furthermore, a sequence of black squares can be seen along the diagonal time scale. The individual squares are interrupted by crossings from the lattices in the colors of the lattice axes. The squares correspond to isoelectric sections (ECG areas without electrical activity). This global structure is of general validity and robust to noise. This is now illustrated in comparison with the constructed, idealized ECG from FIG. 5a/b on a real ECG signal with noise:

FIG. 5c shows the derivation (so-called V5 lead) of a real ECG. The pattern in FIG. 5c has a partly blurred structure. This is clearly visible in the course and the strongly varying width of the yellow axes as well as the less sharply defined black/dark squares. Also, the axes (yellow, cyan, magenta) no longer all meet at one point; the crossing points of the axes often diverge. In addition, no sharply crossing lines are formed (compare area A in FIG. 5a with area A* in FIG. 5c).

Figure 5D:
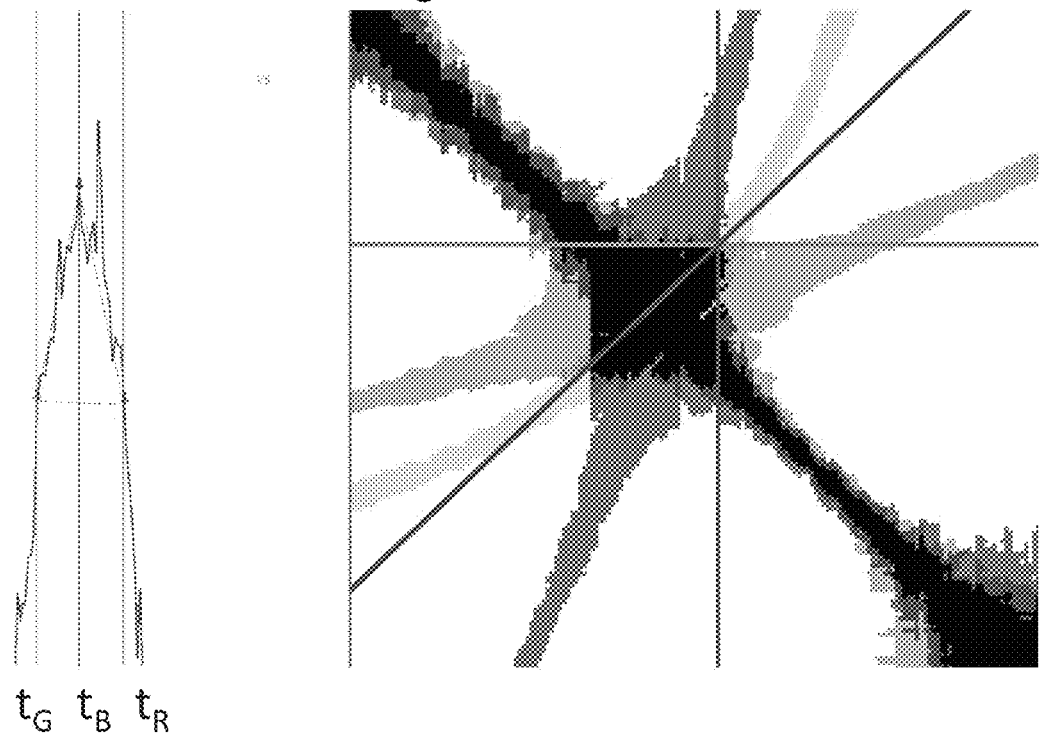

However, these blurs are not due to interference, such as noise or similar, but are characteristics of the real ECG signal and thus indicate deviations from an abstract ideal signal curve. FIG. 5d illustrates that an exact (interference-resistant) analysis is possible by means of the invention: For example, the peak of the fifth T-wave is to be determined. FIG. 5d shows an enlargement of the T-wave. The noise in the time signal (left half of the figure) is clearly visible, which makes an exact signal analysis much more difficult in the time domain. This is because the highest point in the signal is not the peak but a peak in the noise. If, on the other hand, the space-time representation according to the invention (right half of the figure) is considered with respect to a threshold, i.e., a threshold value is set such that all distances below the threshold value are set to zero and above the threshold value are set to 1, or 255, a coherent square can be clearly seen. The upper right corner shows the correct vertex in the signal. The determination does not require any filtering, smoothing, or averaging of the signal as required by conventional methods, e.g., applying approximations to the derivative of the signal, etc. While all of these conventional measures smooth the signal and thus suppress noise, they also invariably cause a shift in the signal. This is not the case with the present method according to the invention. The present method makes use of the global, multi-scale structure in the space-time context of the signal.

FIG. 5e shows another V5 derivative of a real ECG. The relative fluctuation in the peaks of the individual waves and spikes is striking. To determine this fluctuation, it is not only necessary to know the exact location of the vertex but also the relative height of the vertices. This metric relationship is derived from the crossing points on the first secondary diagonal. For this purpose, an amplified section of the time lattice is shown in FIG. 5f. Three consecutive T-waves are considered in each case. At the intersection of the yellow lines (these are labeled "yellow"), the vertices of the two outer T-waves are exactly coincident. The T-wave in the middle, on the other hand, is slightly offset in time and signal strength. Furthermore, the signal in the rising edge is less steep. This alternation in time, signal magnitude and signal morphology is diagnostically relevant and there is a need to determine these criteria as accurately as possible (see technical papers on the so-called "microvolt T-wave alternation" such as the article "Microvolt T-wave Alternans: Where Are We Now?" by L. Aro Aapo, published in the journal "Arrhythmia & Electrophysiology Review" 2015; Vol. 5(1); pages 37-40, or the article "Usefulness of microvolt T-wave alternans testing in the assessment of all-cause mortality and life-threatening ventricular arrhythmia risk in patients with left ventricular dysfunction" by Ludmila Danilowicz-Szymanowicz et al., published in "Arch Med Sci" 2015; Vol. 11, 5; pages 945-951 or also the article "Microvolt T-Wave Alternans" by Richard already mentioned at the beginning. L. Verrier et al.). Compared to the conventional methods, i.e. observation and interpretation of the temporal signal curves similar to a classical curve discussion in mathematics, the invention allows a completely new access to the properties of the measured signals/array of signals and, thanks to a successful representation/visualization of their spatio-temporal coherence for the first time, the invention provides a significant improvement in the exact determination of spatio-temporally relevant changes such as alternances and the like.

Figure 6A:
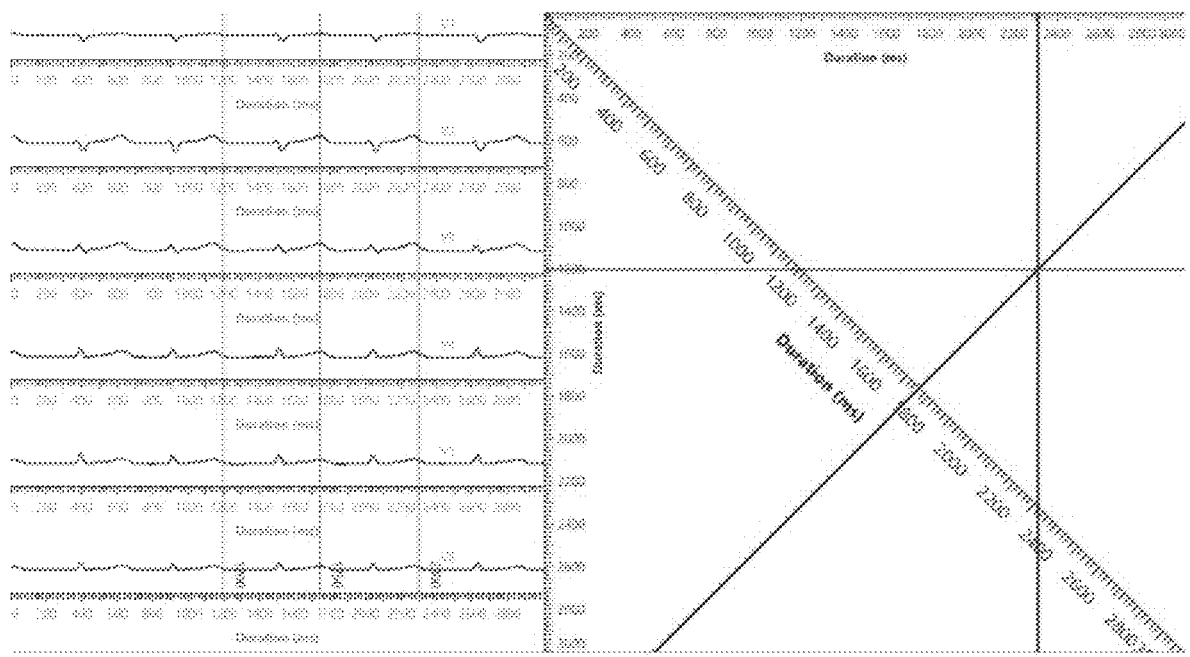
FIGS. 6a and 6b show in detail the patterns forming in the time lattice, here for the analysis of a multi-channel signal (signal array, N=6).
Figure 6B:
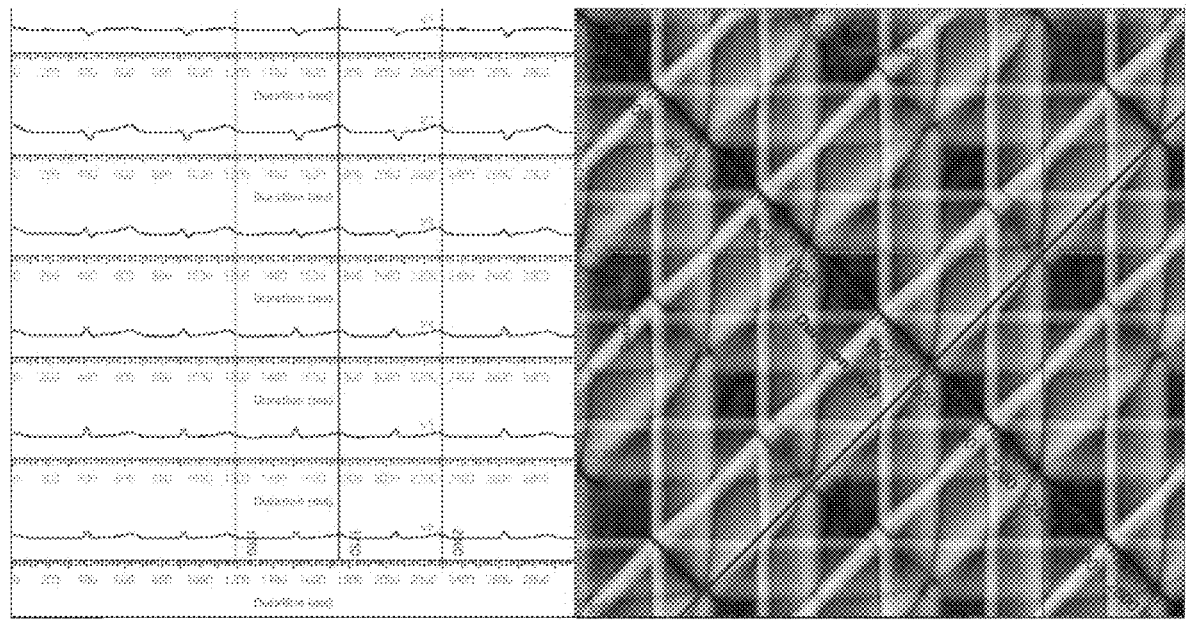

FIGS. 6a and 6b illustrate the structure of a time lattice and the pattern formed therein for a multi-channel ECG signal. Here, too, the pattern has the yellow bars typical of the invention and the cyan- or magenta-colored bars.

Figure 6C:
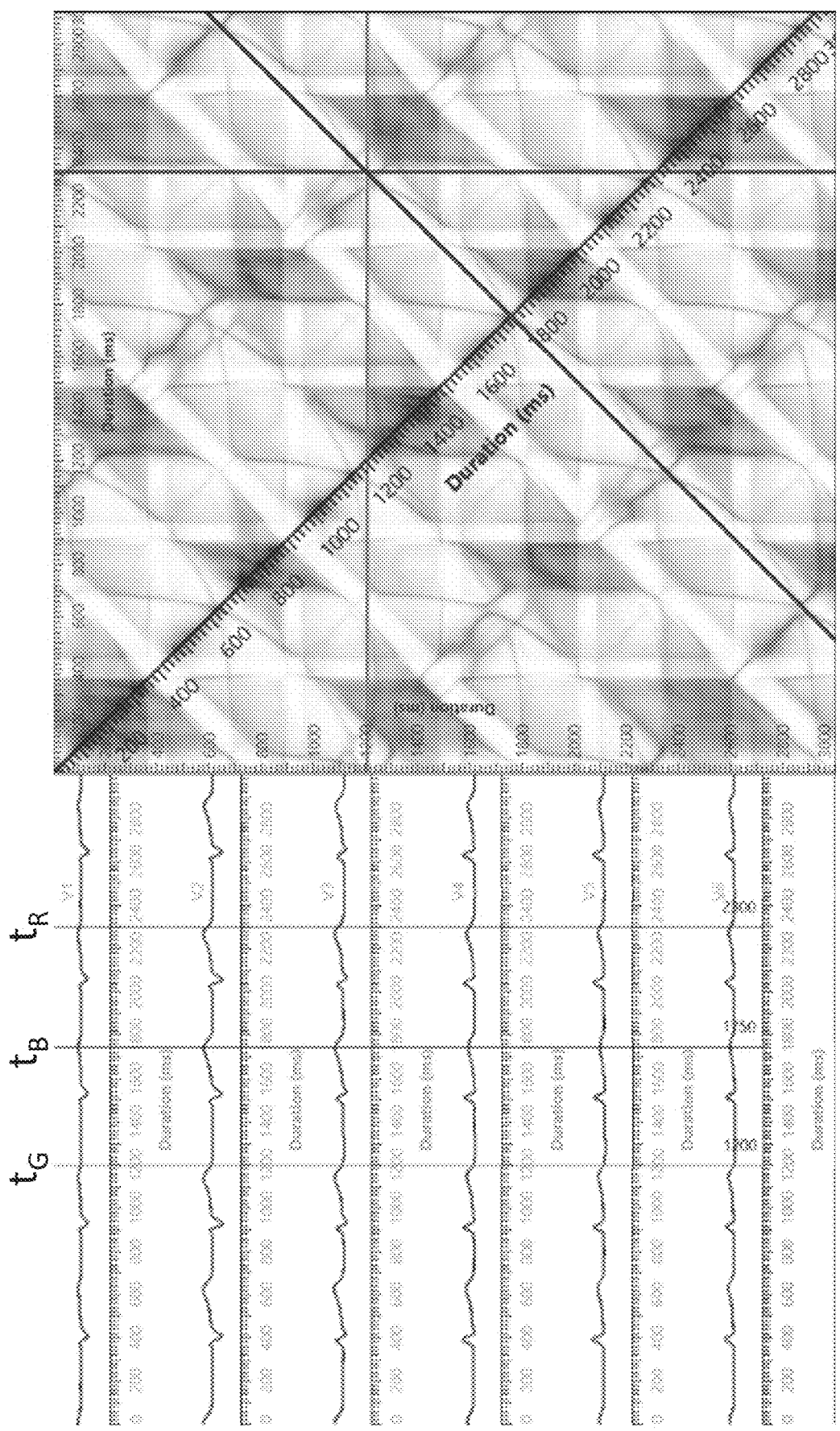
FIG. 6c uses a lighter visualization to show the patterns forming as shown in FIG. 6b.

Compared to FIG. 6b, the FIG. 6c shows the pattern in a lighter representation in order to illustrate that not only the course of the colored bars is of interest for the signal analysis, but also the relative position of the bars to each other and any change that may occur, as well as the areas between the bars. The coding is done by the skeleton of the graph. The skeleton refers to the clearly recognizable line structure of the graph. This forms intersections or crossing points. The relative openness of the intersection points encodes the amount of coherence or variation in the signal. This can be illustrated once again using a simulated signal.

Figure 7:
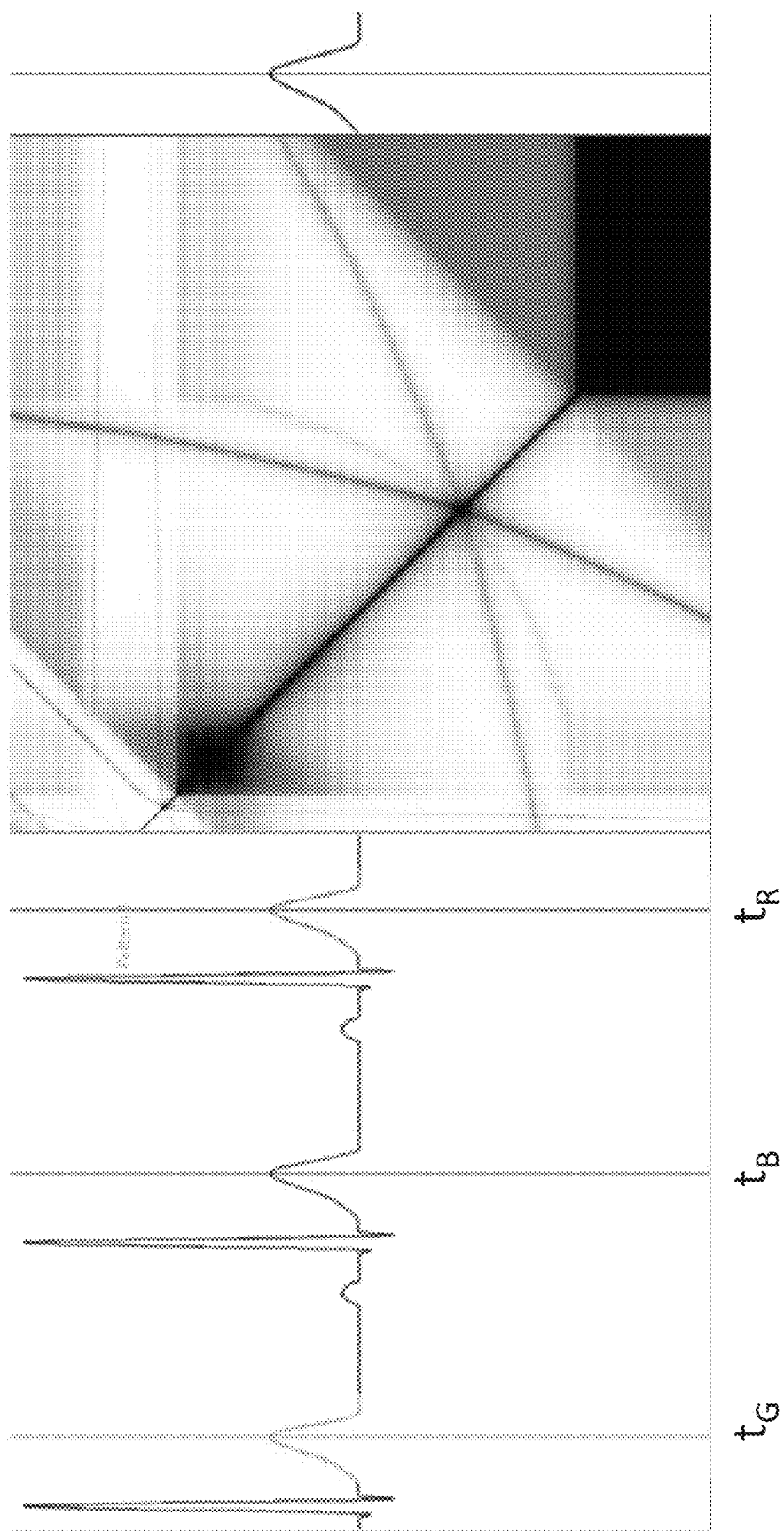
FIG. 7 shows, for comparison with FIG. 5f, an idealized, constructed ECG and the visualization or representation in the time lattice calculated from it.

In FIG. 7, three consecutive heartbeats of an idealized constructed ECG are shown, where the corresponding beats occur at a fixed time offset and the individual beats are congruent. The encoding of three consecutive T-waves in the combinatorial time lattice results in three lines meeting at exactly one point (see the three intersecting lines in cyan, magenta, yellow, and black, with the lines labeled "yellow," "magenta," and "cyan," respectively, for distinguishability). FIG. 7 is to be compared with FIG. 5f, which refers to a real measured ECG. In the case according to FIG. 5f, three deflections are present, which are not at constant intervals in time and are not congruent in their time-voltage characteristics. In this case the black line disappears and the crossing point widens to three separate points. The resulting triangle (see dotted triangle in FIG. 5f) indicates the extent of the spatio-temporal disparity. This is also expressed in the superposition of the three ST complexes shown to the right of the time lattice (compare with FIG. 7).

Figure 8:
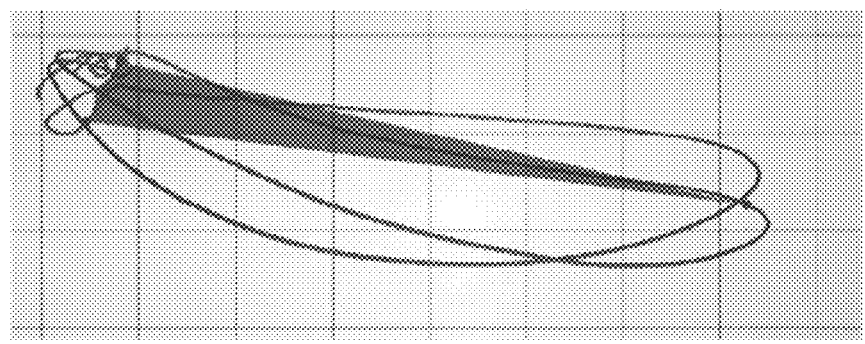
FIG. 8 illustrates the calculation of distances in a so-called VCG loop.

FIGS. 8-10 illustrate that the invention also enables accurate analysis of other ECG features based on the vector cardiogram (VCG). For example, FIG. 8 shows an illustration of a vector cardiogram (VCG) comprising vector loops (VCG loops). The vector cardiogram represents the electrical excitation of the heart using three orthogonal axes whose orientation corresponds to the orientation of the main anatomical axes. Because the heartbeat is cyclic, the individual segments of cardiac excitation show up as delineated loops. The derivation of the VCG can be accomplished by special electrode configurations and circuitry, or the conventional 12-lead ECG can be transformed into the VCG by special mapping. For the evaluation of the VCG related to drug side effects and diseases, for example, the exact definition and determination of the QT time and QRS-T angles is important. For QT time and drug side effects, see, for example, Johannesen at al, Differentiating Drug-Induced Multichannel Block on the Electrocardiogram: Randomized Study of Dofetilide, Quinidine, Ranolazine, and Verapamil, Clinical Pharmacology & Therapeutics, 2014, 96(5), 549-558, for QRS-T angle and risk assessment of sudden cardiac death see e.g. Man et al, "Vectorcardiographic diagnostic & prognostic information derived from the 12-lead electrocardiogram: Historical review and clinical perspective," Journal of Electrocardiology, 2015, 48, 463-475, and Bergfeldt et al, "Spatial peak and mean QRS-T angles: A comparison of similar but different emerging risk factors for cardiac death, Journal of Electrocardiology, 2020, 61, 112-120.

Figure 10A:
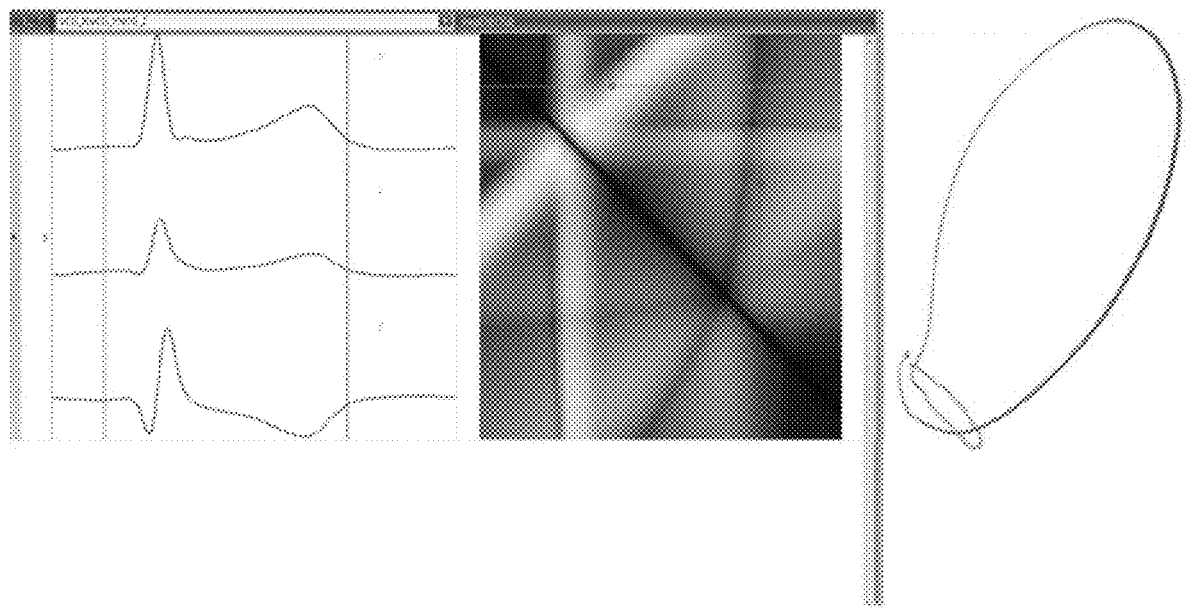
FIGS. 10a, 10b and 10c show in detail the patterns that emerge in the time lattice and illustrate their evaluation in regard to VCG loops.
Figure 10B:
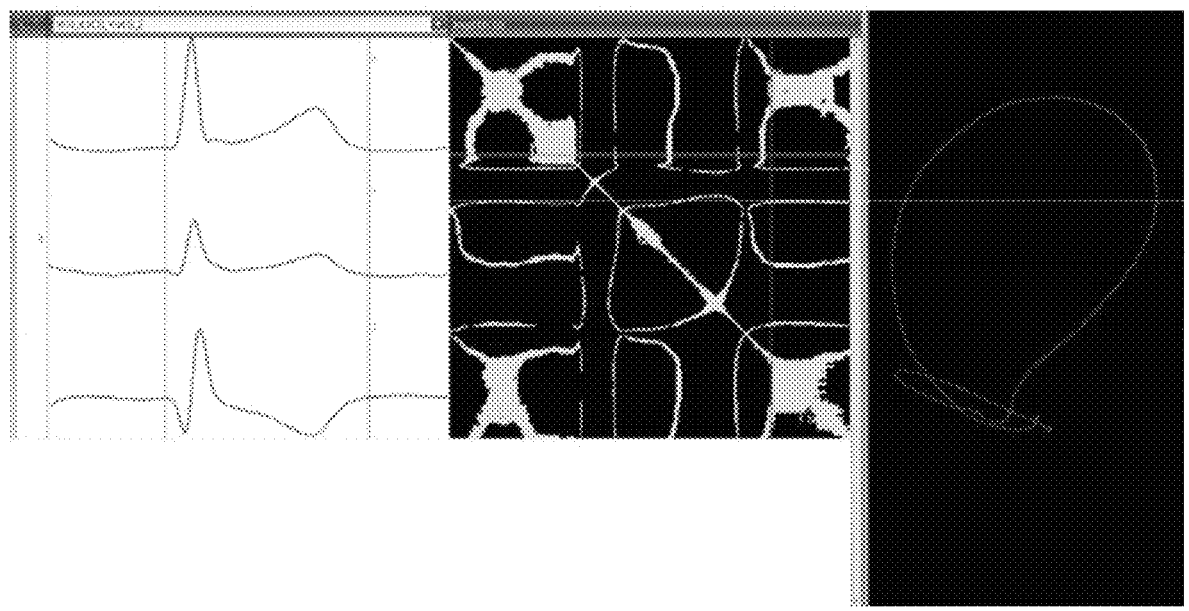
Figure 10C:
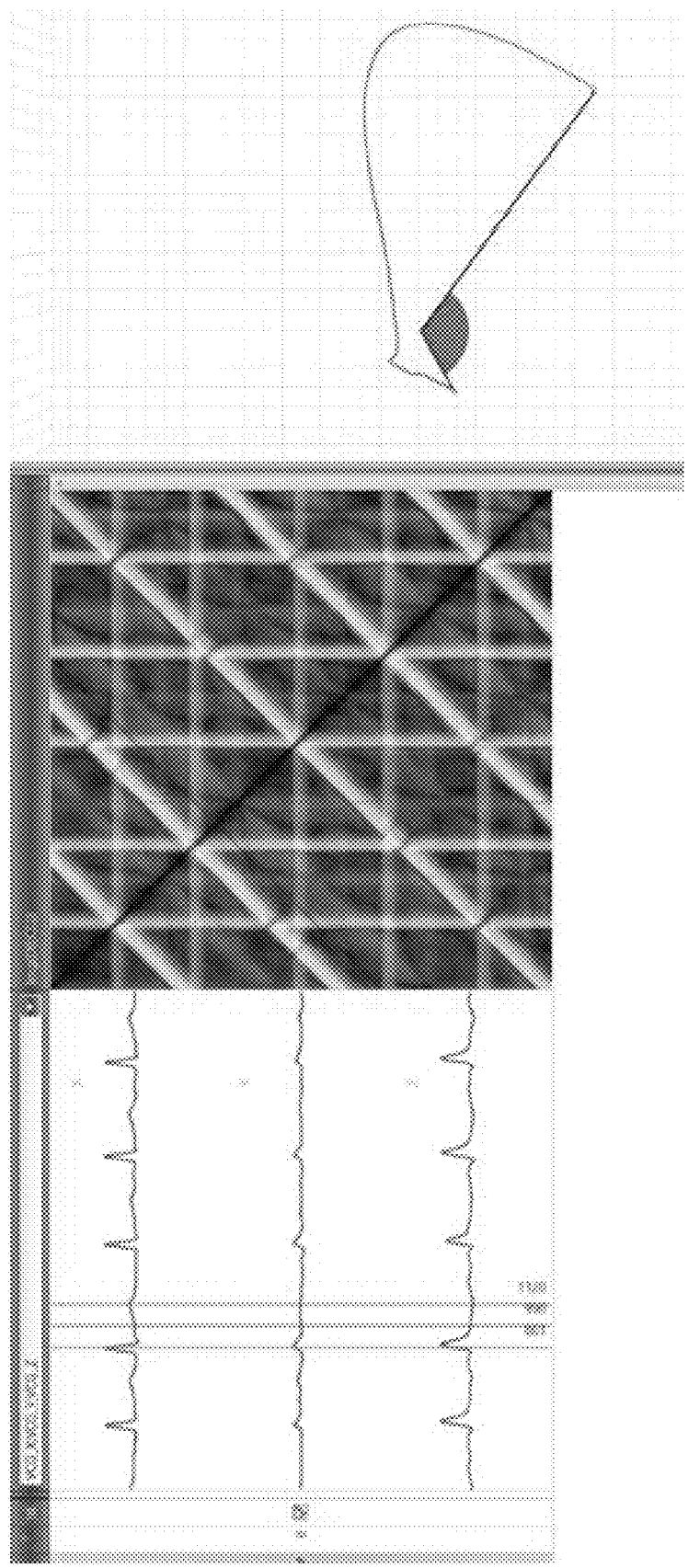

Description of FIG. 10a-c: The QRS complex and the T wave are shown in the vector cardiogram by two loops (see FIGS. 10a and 10b). Depolarization is completed exactly when the QRS loop has closed. Repolarization is completed exactly when the T-loop has closed. The QT time is thus the temporal distance between the two closure points. These can be clearly seen as points in the space-time image, see FIG. 10a and FIG. 10b. The angle between the maximum QRS vector and the maximum T vector of a cardiac cycle is one of the parameters used to assess the risk of sudden cardiac death. The exact determination of the angle is again performed in the space-time image, see FIG. 10c.

The invention is suitable for supporting the analysis of any type of time- and space-dependent signals, and is by no means limited to the exemplary examples described herein.

Figure 12:
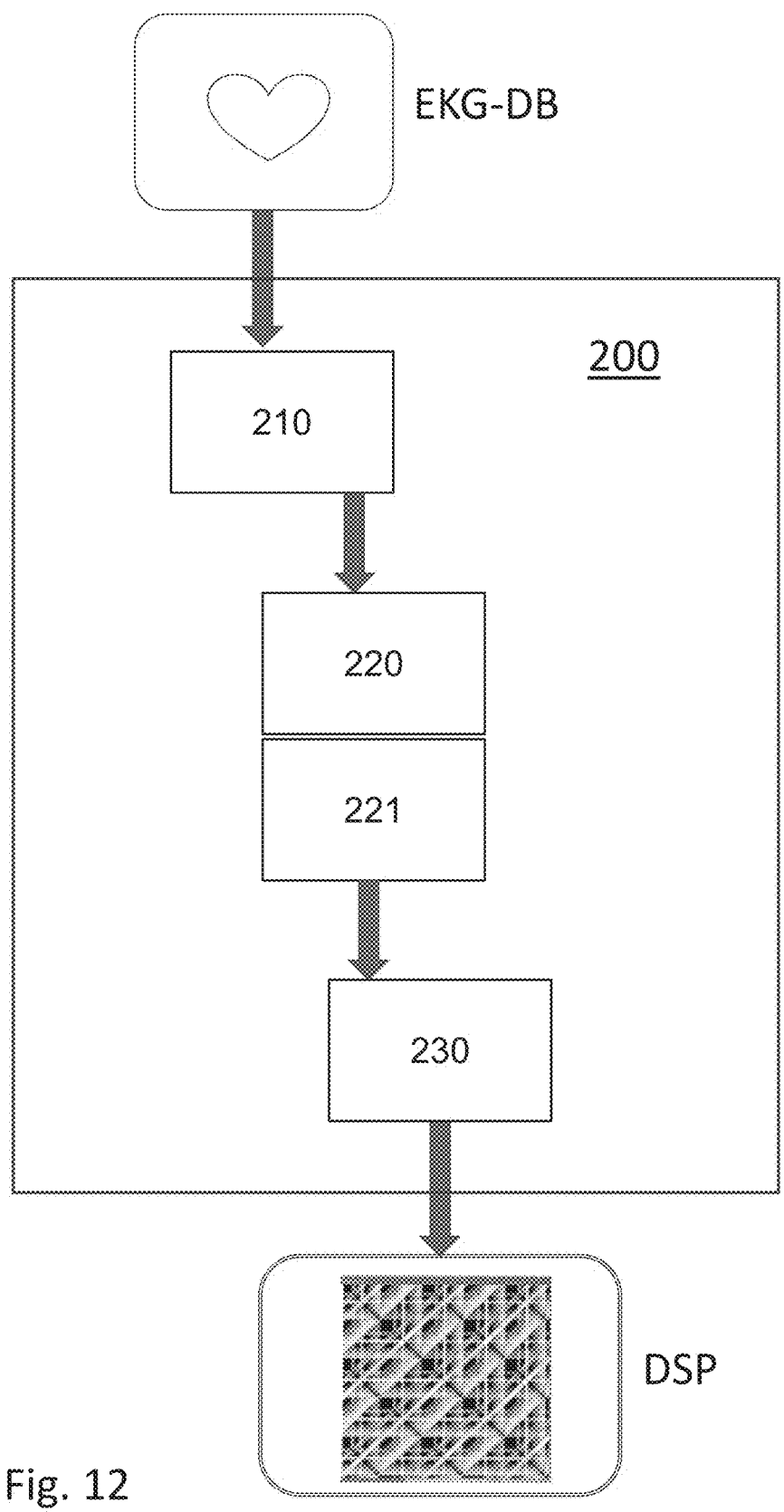
FIG. 12 schematically shows the structure of a device according to the invention.

The invention will now further be described also with reference to FIGS. 11-12, where FIG. 11 illustrates the flow chart for a process 100 according to the invention. FIG. 12 shows the schematic structure of a device 200 carrying out the process, and again with reference to FIGS. 6a-c and FIGS. 10a-c the color coding is again illustrated. The elements shown schematically in FIG. 12 may be implemented in various forms of hardware, software or combinations thereof. Preferably, these elements are implemented in a combination of hardware and software on one or more appropriately programmed general-purpose devices that may include a processor, memory and input/output interfaces. The connections implied by FIG. 12 and described herein is defined to mean directly connected to or indirectly connected with through one or more intermediate components. Such intermediate components may include both hardware and software-based components. It will be appreciated by those skilled in the art that the block diagrams in FIG. 12 and presented elsewhere herein represent conceptual views of illustrative hardware and circuitry embodying the principles of the disclosure. Similarly, any functions or methods implied by the figures of this disclosure may be represented in computer readable media and so executed by a computer or processor, whether or not such computer or processor is explicitly shown.

The method 100 comprises the following steps:

Step 110: Provision of N metrologically recorded, in this case bioelectrical, signals which are single-channel (N=1) or multi-channel (N>1) with respect to a measurement space, in this case the anatomical space, and thus each have a time-dependent and space-dependent signal profile U, the N signals being provided in digitized form and for a predeterminable time period T comprising M time points and being capable of being represented as an M×N matrix MAT with M tuples of N signal values each, the tuples of N signal values detected at the respective time being understood as points in an N-dimensional space. In the case of voltage values, this can also be interpreted as an N-dimensional vector space;

Step 120: acquiring all possible combination of k (k≥2) tuples from the M tuples, where the k tuples are defined as k signal vectors $\vec{U}_1, \ldots, \vec{U}_k$ at k times t1, . . . , tk and for each combination calculating distances of the signal vectors $\vec{U}_1, \ldots, \vec{U}_k$ whereby for each combination $$\binom{k}{2}$$

distance values are calculated, which can be interpreted as edge lengths of a (k−1) simplex SIM, so that a simplex ((k−1)-SIM is assigned to each combination of k time points;

And step 130: coding at least one quantity characteristic of the respective simplex SIM into color values (technical color information/control parameters) COL of a color (color valence CV) and representing the same in a combinatorial time lattice CTL, wherein each lattice point GP of the time lattice represents a combination of k (k≥2) time points, to each of which one of the simplexes ((k−1)-SIM is assigned, wherein each lattice point GP is assigned that color valence CV which has been coded for the assigned simplex ((k−1)-SIM.

If the method is applied for each two (k=2) time points, then this is done by assigning to each combination of two (k=2) time points a 1-simplex, i.e., an edge. Its characteristic measure in its geometrical interpretation is a distance. To each edge its distance is assigned, the characteristic quantity of which indicates the length of the edge, and wherein each lattice point of the time lattice represents a combination of two (k=2) time points, to which one of the edges is assigned in each case, wherein each lattice point is represented with that grey value which has been coded for the assigned edge length. For the case of a 3-dimensional signal space (N=3) see FIG. 9b) which can be represented graphically.

Figure 9A:
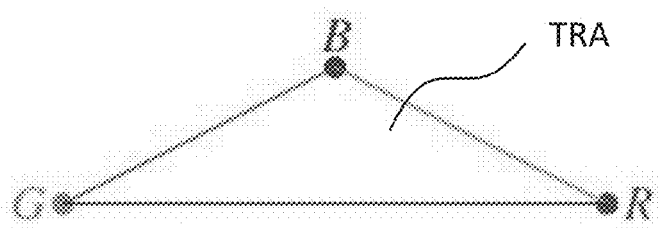
FIGS. 9a and 9b exemplify schematic representations of simplexes, e.g. of a distance triangle, for illustrating the method according to the invention.
Figure 9B:
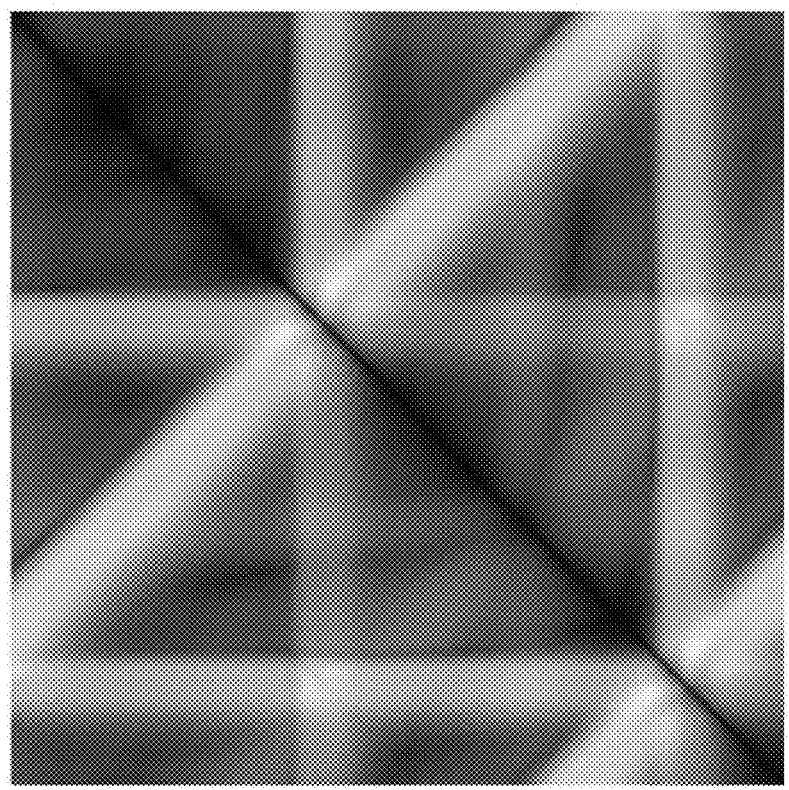

If the method is calculated and coded for three (k=3) time points respectively, then this is done (as also described previously) by assigning to each combination of three (k=3) time points, tG, tB, tR, a 2-simplex (2-SIM), i.e., a simplex in its geometrical interpretation in the form of a triangle (see TRA in FIG. 9a). The characteristic quantities of which comprise the side lengths, angles and/or surface area, and wherein each lattice point LP of the time lattice represents a combination of three (k=3) points in time, tB, tG, tR, to which in each case one of the simplexes SIM, i.e., in this case a triangle, is assigned, wherein each lattice point LP is filled with that color or color valence, respectively, which is to be used for the triangle coding, e.g., coding the three side lengths as RGB values. See FIGS. 9a/b for the case of the 3-dimensional (N=3) signal space, which can be represented graphically in the visual space.

The method can be applied for all cases greater than or equal to 2, e.g., also for k=4. In this case, each combination of four (k=4) time points is assigned a 3-simplex, i.e., a simplex in its geometrical interpretation in the form of a tetrahedron, the characteristic quantities of which comprise the volume content, the side surface (faces) contents, the edge lengths and/or angles, and wherein each lattice point (LP) of the time lattice represents a combination of four (k=4) time points, to each of which one tetrahedron is assigned, wherein each lattice point (LP) is filled with that grey or color value (CV) which has been coded for the assigned tetrahedron, (compare with FIGS. 9a/b) for the case of the 3-dimensional visual space which can be represented graphically.

As also described before, for the case k=3 a 2-simplex is considered, and as characteristic quantity(s) its content, edge lengths and/or angles are calculated and encoded in a color, in particular by means of a predeterminable colorimetry. For encoding, the length values g, b, r of each combination corresponding to the edge lengths of the 2-simplex are normalized according to a predeterminable range of values, e.g. 000, . . . , 255, to normalized values g*, b*, r*, and are subsequently encoded as color valence using the predeterminable color metric according to the selected color space. In the examples described, the time points have been set so that the three time points tG, tB, tR of each combination are equidistantly spaced apart. However, this does not have to be the case; it can also be useful to place the intermediate time point (see FIG. 3a) not exactly in the middle between the two other time points, but offset from them; in this way phase shifts (T-wave alternance) can be analyzed even better.

On the input side, the device 200 can be connected to, for example, a database ECG-DB or an ECG device from which the data of numerous bioelectrical signals can be retrieved. On the output side, the device 200 can be connected to a screen or display DSP or the like on which the time lattice with the calculated image data is displayed.

The device 200 itself may be implemented by a computer or personal computer and includes first means (unit) 210 for providing N signals or data series, in particular concerning bioelectrical signals (e.g., ECG, EEG, APs . . . ), which have been acquired in a single-channel (N=1) or multi-channel (N>1) manner with respect to a measurement space, in particular an anatomical space (head (sculp, brain), torax (limbs, body surface, heart (endocard, epicard)), and thus each have a time- and space-dependent signal characteristic, the N signals being provided in digitized form and for a predeterminable time period with M time points as data tuples of N signal values in the value range. These first means (unit) 210 thus carry out the step 110 of the method and may be implemented in particular by a storage medium/data memory to store the data of the N bioelectric signals retrieved from the ECG-DB/EEG-DB/physiology-DB database.

Further, the device 200 includes second means (unit) 220 for acquiring all possible combinations of k (k≥2) tuples from the M tuples with their signal values (U1, . . . , UN) at k out of M time points t1, . . . , tk. Also, the second means (unit) 220 serves to compute, for each combination, distances of the signal tuples (U1, . . . , UN), whereby for each combination $$\binom{k}{2}$$

spacing values $$\left(a_1, \ldots, a_{\binom{k}{2}}\right)$$

are calculated, which are interpretable as edge lengths of a (k−1)-simplex ((k−1)-SIM), such that a simplex is associated with each combination of k time points. These second means (unit) 220 thus carry out the step 120 of the method and can be implemented in particular by a computer or microprocessor which processes the data of the N bioelectric signals stored in the data memory 210 and calculates distance values therefrom.

Also, the device 200 comprises third means (unit) 221 for coding at least one quantity characteristic of the respective simplex SIM into color values of a corresponding color valence CV. These third means (unit) 221 thus carry out the sub-step 131 of the method and may be implemented, in particular, by the above computer or microprocessor which further processes the previously calculated distance values and calculates therefrom color values. The second and third means (units) 220 and 221, respectively, can be realized by a computing unit of the computer.

Moreover, the device 200 or the computer comprises fourth means (unit) 230 for representing the coded color values COL or color valence in a combinatorial time lattice CTL, each lattice point GP of the time lattice representing a combination of k (k≥2) time points (t1, . . . , tk) to each of which one of the simplexes SIM is associated, each lattice point GP being represented with the color or color valence that has been coded for the associated simplex SIM. These fourth means (unit) 230 thus carry out the sub-step 132 of the method and can be implemented, in particular, by a graphics card which is controlled with the data of the previously calculated colors or color values in order to then cause the display on the screen DSP.

The invention can be used in many fields of application. The signals acquired by measurement and having a time- and space-dependent signal characteristic can be provided in particular as digitized signal data, and can belong, for example, to one of the following groups: To the group of bioelectrical signals or signal data, in particular concerning electrocardiograms, electroencephalograms, electrooculograms, electromyograms, and cell membrane action potentials (as described above) or, for example, to the group of seismographic signals or signal data. Also, instead of the metrologically recorded signals N relating to an observation or measurement space, data series can be provided which relate to an observation space and belong, for example, to one of the following groups: demographic data series, epidemiological data series, or economic data series, in particular financial data series (e.g. stock market prices). The invention provides a completely new signal or data processing for visualization in the form of a combinatorial time lattice, in which characteristics/patterns relating to the spatio-temporal coherence of the acquired and processed signals or data are clearly and immediately recognizably displayed to the user.

The invention also relates to a computer program product comprising instructions which, when executed by the computer 200, cause the computer to perform the method according to the invention. In addition, the invention relates to a computer-readable storage medium comprising instructions which, when executed by the computer, cause the computer to perform the method according to any one of the preceding method claims.

What is claimed is:

1. A device (200) for providing technical support for the analysis of signals acquired by measurement, the signals having a time- and space-dependent signal characteristic, the device having the following functional means:
   first means/unit (210) for providing N signals that have been acquired in a single-channel (N=1) or multi-channel (N>1) manner with respect to an observation space and thus each have a time-dependent and space-dependent signal characteristic (U), the N signals being provided in digitized form and for a predeterminable time period T comprising M time points and being capable of being represented as an M×N matrix (MAT) with M tuples of N signal values each, the N signal values acquired at the respective time t forming an N-dimensional signal vector $\vec{U}_t$ in an N-dimensional signal space;
   second means/unit (220) for acquiring all possible combinations of k(k≥2) tuples from the M tuples by acquiring k signal vectors $\vec{U}_1, \ldots, \vec{U}_k$ at k time points, and for each combination calculating all possible distances of the tuples from each other, whereby for each combination $$\binom{k}{2}$$

distance values (in case k=3, i.e. r, g, b) are calculated which are interpretable as edge lengths of a (k−1) simplex (SIM), such that each combination of k time points (in case k=3, i.e. $t_B$, $t_G$, $t_R$) is associated with a simplex (SIM);
   third means/unit (221) for coding at least one quantity characteristic of the respective simplex (SIM) into color values (COL) of a color/color valence CCV) on the basis of a color metric, and
   fourth means/unit (230) for displaying the color/color valence (CV) in a combinatorial time lattice (CTL), each lattice point (GP) of the time lattice representing a combination of k (k≥2) time points (in case k=3, i.e. $t_B$, $t_G$, $t_R$) each associated with one of the simplexes (SIM), each lattice point (GP) being represented with that color/color valence (CV) which has been encoded for the associated simplex (SIM).

2. The device (200) of claim 1,
   wherein k=3, whereby each combination of three (k=3) time points ($t_G$, $t_B$, $t_R$) is associated with a 2-simplex (SIM), i.e. a polytope in the form of a triangle (SIM), the characteristic quantities of which comprise the area, the side lengths and/or angles, and wherein each lattice point (GP) of the time lattice (CTL) represents a combination of three (k=3) time points ($t_G$, $t_B$, $t_R$), to each of which one of the triangles (SIM) is assigned, wherein each lattice point (GP) is represented with that color valence (CV) which has been coded for the assigned triangle (SIM).

3. The device (200) of claim 1,
   wherein k=4, whereby each combination of four (k=4) time points is associated with a 3-simplex, i.e. a polytope in the form of a polyhedron (e.g. of a tetrahedron), whose characteristic quantities comprise the volume contents, the area contents, the side lengths and/or angles, and wherein each lattice point (GP) of the time lattice (CTL) represents a combination of four (k=4) time points, to each of which one of the tetrahedra is assigned, wherein each lattice point (GP) is represented with that color/color valence (CV) which has been coded for the assigned polyhedron.

4. The device (200) of claim 2, wherein the at least one characteristic quantity of the respective triangle (SIM) is represented by its area, side lengths and/or angle which is coded to color values/a color valence (CV), in particular by means of a predeterminable colorimetry.

5. The device (200) of claim 2, wherein for coding the distance values (g, b, r) of each combination, which also correspond to the side lengths of the triangle (SIM), are normalized according to a predeterminable value range (000, . . . , 255) to normalized values (r*, g*, b*) and are subsequently coded by means of the predeterminable colorimetry to the color values (COL), in particular to corresponding color values of color primaries/basis vectors of the color valence (CV).

6. The device (200) of claim 2, wherein the respective three time points ($t_G$, $t_B$, $t_R$) of each combination are equidistantly spaced apart.

7. The device (200) of claim 1, wherein the combinatorial time lattice (CTL) comprises at least two orthogonal time axes each relating to one of the three time points ($t_G$, $t_B$, $t_R$).

8. The device (200) of claim 1, wherein the device is implemented by a computer, wherein the first means/unit (210) is realized by a storage medium of the computer, the second and third means/units (220, 221) are realized by a computing unit (CPU) accessing the storage medium and/or a graphics processing unit (GPU) of the computer driven by the computing unit, and the fourth means/unit (230) is realized by the graphics processing unit driven by the computing unit of the computer.

9. The device (200) of claim 1, wherein the signals acquired by measurement and having a time- and space-dependent signal characteristic are provided in particular as digitized signal data, and belong to one of the following groups:
   bioelectrical signals or signal data, in particular relating to electrocardiograms, electroencephalograms, electrooculograms, electromyograms and/or cell membrane action potentials, the observation space being the anatomical space of one or more patients; or
   seismographic signals or signal data, the observation space being the hydrogeological space of one or more geographical areas.

10. The device (200) of claim 1, wherein k=2, whereby each combination of two (k=2) time points is associated with a 1-simplex, i.e. a polytope in the form of a line, the characteristic size of which indicates the length of the line, and wherein each lattice point of the time lattice represents a combination of two (k=2) time points, each of which is associated with one of the lines, each lattice point being represented with an achromatic color valence which has been encoded for the associated line.

* * * * *